United States Patent
Stahl et al.

(10) Patent No.: US 12,409,115 B2
(45) Date of Patent: Sep. 9, 2025

(54) SUNSCREEN COMPOSITION COMPRISING VISIBLE LIGHT PROTECTING AGENTS AND METHODS OF USE

(71) Applicant: DOC MARTIN'S OF MAUI, Kihei, HI (US)

(72) Inventors: Christopher Ryan Stahl, Pioneertown, CA (US); Curtis Allan Cole, New Holland, PA (US); George Michael Martin, Kula, HI (US)

(73) Assignee: DOC MARTIN'S OF MAUI, Kihei, HI (US)

( * ) Notice: Subject to any disclaimer, the term of this patent is extended or adjusted under 35 U.S.C. 154(b) by 161 days.

(21) Appl. No.: 18/227,489

(22) Filed: Jul. 28, 2023

(65) Prior Publication Data

US 2024/0058237 A1  Feb. 22, 2024

Related U.S. Application Data

(60) Provisional application No. 63/396,769, filed on Aug. 10, 2022.

(51) Int. Cl.
| | |
|---|---|
| *A61K 8/29* | (2006.01) |
| *A61K 8/19* | (2006.01) |
| *A61K 8/26* | (2006.01) |
| *A61K 8/27* | (2006.01) |
| *A61Q 17/04* | (2006.01) |

(52) U.S. Cl.
CPC ............... *A61K 8/29* (2013.01); *A61K 8/19* (2013.01); *A61K 8/26* (2013.01); *A61K 8/27* (2013.01); *A61Q 17/04* (2013.01); *A61K 2800/31* (2013.01); *A61K 2800/621* (2013.01); *A61K 2800/651* (2013.01)

(58) Field of Classification Search
None
See application file for complete search history.

(56) References Cited

U.S. PATENT DOCUMENTS

| | | |
|---|---|---|
| 6,972,129 B1 | 12/2005 | Ogawa et al. |
| 2007/0274932 A1 | 11/2007 | Suginaka et al. |
| 2008/0025932 A1 | 1/2008 | Bissett et al. |
| 2015/0306017 A1* | 10/2015 | Fanizza ............ A61K 8/23 424/59 |
| 2017/0266470 A1 | 9/2017 | Liu et al. |
| 2018/0296455 A1 | 10/2018 | Blachechen et al. |
| 2019/0290560 A1 | 9/2019 | Singleton |

FOREIGN PATENT DOCUMENTS

| | | |
|---|---|---|
| WO | 2009/079135 A2 | 6/2009 |

OTHER PUBLICATIONS

Rodriquez, Kari (Authorized PCT Officer), Transmittal of the International Search Report and the Written Opinion of the International Searching Authority, or the Declaration issued Jan. 10, 2024 in corresponding International Application No. PCT/US2023/028948, 12 pages.

Cole et al., "Evaluating Sunscreen Ultraviolet Protection Using a Polychromatic Diffuse Reflectance Device," Photodermatol Photoimmunol Photomed. 2019;35:436-441.

* cited by examiner

*Primary Examiner* — Nannette Holloman
(74) *Attorney, Agent, or Firm* — MH2 Technology Law Group LLP

(57) ABSTRACT

Provided herein is a method of reducing or preventing sunburn caused from visible and ultraviolet radiation in a subject, the method comprising topically applying to the subject a sunscreen composition comprising at least one inorganic UV filtering agent selected from zinc oxide or titanium dioxide; at least one inorganic pigment selected from iron oxide; and at least two visible light protecting agents comprising barium sulfate and mica; wherein the at least two visible light protecting agents are present in an amount effective to reduce or prevent sunburn caused from visible light. Also provided herein are sunscreen compositions and methods of increasing the visible light protection factor of a sunscreen composition.

20 Claims, 4 Drawing Sheets

SUNSCREEN COMPOSITION COMPRISING VISIBLE LIGHT PROTECTING AGENTS AND METHODS OF USE

CROSS-REFERENCE TO RELATED APPLICATION

This application claims the benefit of, and relies on the filing date of, U.S. provisional patent application No. 63/396,769, filed 10 Aug. 2022, the entire disclosure of which is incorporated herein by reference.

DETAILED DESCRIPTION

Field of Disclosure

Disclosed herein are compositions for topical sun protection comprising at least one inorganic UV filtering agent, at least one inorganic pigment, and a combination of at least two visible light protecting agents. The compositions disclosed herein may be used to protect against both visible light-induced erythema and ultraviolet radiation-induced erythema.

BACKGROUND

The electromagnetic spectrum is a spectrum comprising the range of frequencies of electromagnetic radiation and its associated wavelengths, spanning from the lowest wavelength radio waves to the highest wavelength gamma ionizing radiation waves. Beginning with the lowest frequency waves, the spectrum is divided into the following bands: radio waves, microwaves, infrared, visible light, ultraviolet, X-rays, and gamma rays. Initially, only visible light, which has corresponding wavelengths ranging from about 400 nm to about 700 nm, was known to exist. In 1801, however, the UV portion of the electromagnetic spectrum, having corresponding wavelengths ranging from about 10 nm to about 400 nm, was discovered by Johann Ritter to be photochemically and photobiologically active. The most common source of UV light is the sun, and it is the radiation originating from UV light that is responsible for what is commonly referred to as "sunburn" or "erythema." The UV band of the electromagnetic spectrum itself contains a sub-spectrum of three bands: UVA (about 320-400 nm), UVB (about 280-320 nm), and UVC (about 100-280 nm).

Sunburn is a reddening of the skin resulting from prolonged exposure to the sun. The severity of sunburn can range from mild to severe, based on several factors including the length of exposure, intensity of exposure, and an individual's skin type, with fair skin being at a greater risk. Sunburn is a well-recognized risk factor for skin cancer.

The Fitzpatrick skin typing system is a commonly used system by which the tendency of a person's skin to burn or tan when exposed to sunlight may be predicted. Fitzpatrick et al., *The Validity and Practicality of sun-reactive skin types I through VI*, ARCHIVES OF DERM. 1988, 124(6):869-871. Under the Fitzpatrick skin typing system, skin may be categorized into one of six skin types, wherein Type I skin is pale and typically burns without tanning, while Type II skin usually burns and tans less than average or with difficulty. Type III skin tans an average amount with only mild burning, and Type IV skin rarely burns while tanning with ease. Types V and VI refer to brown and black skin, respectively, that rarely or never burns. Fitzpatrick skin types may be used to help predict a person's risk of skin cancer due to sun exposure, wherein the highest risk of skin cancer is observed in people with the fairest skin (i.e., Type I or Type II skin). People with Type III-VI skin may also seek protection from visible light, in order to prevent darkening and worsening of dyschromias such as melasma.

Until recently, it was thought that sunburn was caused exclusively by light in the UV wavelength range (i.e., from 10-400 nm), with no meaningful contribution to sunburn from visible light wavelengths (i.e., above 400 nm). The UV-induced erythema commonly known as sunburn was considered to be induced by direct absorption damage to specific chromophores (primarily DNA) and other proteins in the epidermis and dermis, cause by exposure to UVB radiation, as well as by indirect damage by photo-oxidative processes caused by UVB and UVA radiation. For UVA-induced photo-oxidative damage, the radiation energy absorbed causes oxygen to rise to a triplet or singlet excited energy level, making it capable of interacting with and damaging other surrounding cellular structures, and ultimately resulting in erythema of the skin when present in sufficient quantities.

Action spectra were derived to describe the precise amounts of radiation required to cause erythema at each specific wavelength and have been reported as covering the wavelength range from around 250-400 nm. All published action spectra for erythema stop precisely at 400 nm, with the implication being that wavelengths above 400 nm were of no consequence and had no contribution to the erythema reaction. See, e.g., Schmalwieser, A. et al., *A library of action spectra for erythema and pigmentation*, PHOTOCHEM. PHOTOBIOL. SCI. 2012; 11(2):252-268.

Recently, it was discovered that this assumption is incorrect, and that the visible light portion of the electromagnetic spectrum, and particularly the violet and/or blue light region from about 400-500 nm, can and does have an impact on the induction of erythema, particularly when considering outdoor sun exposures where the sun produces copious amounts of visible light (e.g., 50%) compared with the relatively minor (e.g., 5%) amount of ultraviolet light at terrestrial levels. For example, Zastrow and colleagues demonstrated that free radicals (excited oxygen molecules) can be generated in skin tissue by wavelengths across the ultraviolet and the entire visible light spectrum. When combining the action spectrum with the terrestrial solar spectrum, it was estimated that as much as 50% of the free radicals generated by sunlight are caused by the visible portion of the sun's spectrum, and the other 50% from the ultraviolet portion. Zastrow, L. et al., *The missing link, light (280-1600 nm) induced free radical formation in human skin*, SKIN PHARMACOL. PHYSIOL. 2009; 22:31-34.

Nonetheless, the active ingredients in traditional sunscreen products typically aim only to filter UV rays (primarily UVA and UVB), and are not concerned with the effects of visible light. Typical UV absorbers in sunscreen products may be either organic (e.g., avobenzone, oxybenzone, octyl methoxycinnamate, etc.) or inorganic (i.e., titanium dioxide, zinc oxide, etc.). Manufacturers of these products have worked arduously to produce non-visible sunscreen products, as many consumers do not want to have the sunscreen visible on their skin. While zinc oxide and titanium dioxide are widely used for sunscreen products since around 1987, they are typically incorporated into sunscreen products using very small particles sizes, such as nanosized particles. Nanosized particles may minimize the visible appearance of the zinc oxide and titanium dioxide, making the sunscreen product virtually invisible on the skin after application, while still functioning to absorb the harmful effects of UV radiation from the sun. See Cole C. et al.,

*Metal oxide sunscreens protect skin by absorption, not by reflection or scattering*, PHOTOMED. PHOTOIMMUNOL. PHOTODERMATOL. 2016, 32:1, 5-10.

The nano-particle sized zinc oxide and titanium dioxide may still function as UV filters, as they still operate as semi-conducted absorbers of UV radiation below about 370-380 nm, depending on their band-gap energy. Nonetheless, nano-particle sized zinc oxide and titanium dioxide largely do not scatter and reflect radiation as well above these wavelengths because of their micronized/nano-particle size. Thus, even these inorganic base sunscreens offer little to no protection against radiation in the visible light portion of the electromagnetic spectrum, and may offer diminished protection for wavelengths at the higher end of the UVA spectrum (e.g., 375-400 nm).

Iron oxide may be added to sunscreen products to provide broad protection against both UV and visible light, as it is a known visible light absorber. Iron oxide, however, exists in yellow, red, and brown hues that increase as an increasing amount of iron oxide is added to a sunscreen composition. Accordingly, a sunscreen composition comprising a high concentration of iron oxides, or a concentration effective to protect against visible light, may be undesirable for a person having Type I or II skin, i.e., a person most in need of a visible-light protection to decrease their risk of skin cancer erythema and skin aging effects.

Therefore, there is a need for a sunscreen composition that provides protection against both the UV radiation in sunlight and also the visible light portion of the sun's spectrum, wherein the sunscreen is an acceptable shade for a person with fair to light colored skin. Ideally, such a sunscreen composition should be consumer-acceptable in appearance and provide greater protection to the skin against erythema than conventional UV-only protection sunscreen products.

SUMMARY

Disclosed herein are sunscreen compositions and methods of using sunscreen compositions to reduce or prevent sunburn caused from both visible light and ultraviolet (UV) radiation, as well as methods of increasing the sunscreen protection factor (SPF) and/or the visible light protection factor of the sunscreen composition.

In certain embodiments, disclosed herein is a sunscreen composition comprising (a) at least one inorganic UV filtering agent selected from zinc oxide or titanium oxide; (b) at least one inorganic pigment selected from iron oxide; and (c) at least one visible light protection agent, such as barium sulfate, wherein the at least one visible light protecting agent is present in an amount effective to reduce or prevent sunburn caused from visible light. In certain embodiments, disclosed herein is a sunscreen composition comprising (a) at least one inorganic UV filtering agent selected from zinc oxide or titanium oxide; (b) at least one inorganic pigment selected from iron oxide; and (c) at least two visible light protecting agents comprising barium sulfate and mica, wherein the at least two visible light protecting agents are present in an amount effective to reduce or prevent sunburn caused from visible light.

In certain embodiments, the sunscreen compositions disclosed herein are anhydrous. In certain embodiments, the barium sulfate in the sunscreen composition is present in an amount ranging from about 0.1% to about 10%, such as, for example, from about 1% to about 5%, from about 2% to about 3%, about 5%, or about 2.5%, by weight based on the total weight of the composition. In certain embodiments, the mica in the sunscreen composition is present in an amount ranging from about 0.1% to about 10%, such as, for example, from about 1% to about 5%, from about 2% to about 3%, about 5%, or about 2.5%, by weight based on the total weight of the composition. In certain embodiments, both the barium sulfate and the mica are each present in the sunscreen composition in an amount of about 1% to about 5%, such as from about 2% to about 3%, about 5%, or about 2.5%, by weight relative to the total weight of the composition. In further embodiments of the disclosure, the sunscreen compositions do not comprise an organic UV filtering agent.

In certain embodiments of the disclosure, the sunscreen composition comprises both zinc oxide and titanium oxide, and in certain embodiments, the iron oxide is chosen from the group consisting of black iron oxide, brown iron oxide, red iron oxide, yellow iron oxide, and mixtures thereof. In certain embodiments, at least one of the at least two visible light protecting agents further comprise a coating, such as a silica coating, and in certain embodiments, both the mica and the barium sulfate comprise a coating, such as a silica coating.

In certain embodiments of the sunscreen composition disclosed herein, the iron oxide is present in the sunscreen composition in an amount ranging from about 0.1% to about 10%, such as from about 1% to about 5%, about 1% to about 3%, or about 2% to about 3%. In certain embodiments, the at least one inorganic UV filtering agent is titanium dioxide, and in certain embodiments, the titanium dioxide has a mean particle size ranging from about 5 nm to about 20 nm. In certain embodiments, the at least one UV filtering agent is zinc oxide, and in certain embodiments, the zinc oxide has a mean particle size ranging from about 10 nm to about 100 nm.

In certain embodiments, the sunscreen composition disclosed herein further comprises at least one antioxidant, such as at least one antioxidant selected from the group consisting of vitamin E or derivatives thereof and vitamin C or derivatives thereof. In certain embodiments, the at least one antioxidant is present in the sunscreen composition in a total amount ranging from about 0.1% to about 5% by weight relative to the total weight of the sunscreen composition.

Also disclosed herein is a method of reducing or preventing sunburn caused from visible light and ultraviolet (UV) radiation in a subject, comprising topically applying to the subject a sunscreen composition as disclosed herein, such as a sunscreen composition comprising (a) at least one inorganic UV filtering agent selected from zinc oxide or titanium oxide; (b) at least one inorganic pigment selected from iron oxide; and (c) at least one visible light protecting agent, such as barium sulfate, wherein the at least one visible light protecting agent is present in an amount effective to reduce or prevent sunburn caused from visible light. In certain embodiments, disclosed herein is a method of reducing or preventing sunburn caused from visible light and ultraviolet (UV) radiation in a subject, comprising topically applying to the subject a sunscreen composition as disclosed herein, such as a sunscreen composition comprising (a) at least one inorganic UV filtering agent selected from zinc oxide or titanium oxide; (b) at least one inorganic pigment selected from iron oxide; and (c) at least two visible light protecting agents comprising barium sulfate and mica, wherein the at least two visible light protecting agents are present in an amount effective to reduce or prevent sunburn caused from visible light.

Further disclosed herein are methods of increasing a visible light protection factor of a sunscreen composition as disclosed herein, such as a sunscreen composition comprising (a) at least one inorganic UV filtering agent selected from zinc oxide or titanium oxide; (b) at least one inorganic pigment selected from iron oxide; and (c) at least one visible light protecting agent, such as barium sulfate, wherein the at least one visible light protecting agent is present in the sunscreen composition in an amount effective to increase the visible light protection over an electromagnetic wavelength spectra spanning from about 400 nm to about 800 nm, such as from about 400 nm to about 500 nm. In certain embodiments of the methods disclosed herein, the visible light protection factor is increased by an amount of at least about 0.5, such as at least about 0.7, at least about 0.8, or at least about 0.9, i.e., the visible light protection factor may increase, for example, from about 2.7 to about 3.2, indicating an increase of about 0.5. In certain embodiments, disclosed herein are methods of increasing a visible light protection factor of a sunscreen composition as disclosed herein, such as a sunscreen composition comprising (a) at least one inorganic UV filtering agent selected from zinc oxide or titanium oxide; (b) at least one inorganic pigment selected from iron oxide; and (c) at least two visible light protecting agents comprising barium sulfate and mica, wherein the at least two visible light protecting agents are present in the sunscreen composition in an amount effective to increase the visible light protection over an electromagnetic wavelength spectra spanning from about 400 nm to about 800 nm, such as from about 400 nm to about 500 nm. In certain embodiments of the methods disclosed herein, the visible light protection factor is increased by an amount of at least about 0.5, such as at least about 0.7. at least about 0.8, or at least about 0.9.

It is to be understood that both the foregoing general description and the following detailed description are exemplary and explanatory only and are not restrictive of the present teachings, as claimed.

DESCRIPTION OF THE EMBODIMENTS

Figure 1:
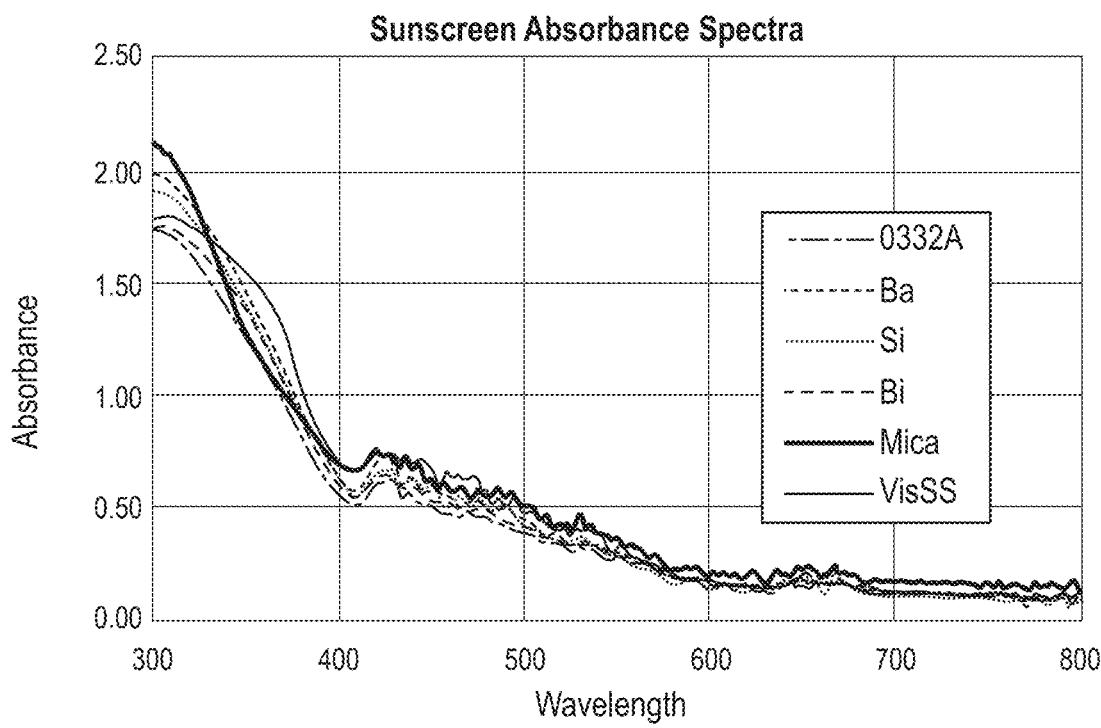
FIG. 1 is graph showing the absorbance of six sunscreen formulations, as described in Example 1, across the UV and visible light spectrum (300-800 nm) of the electromagnetic spectrum.

Reference will now be made in detail to embodiments of the present teachings. In the following description, reference is made to exemplary embodiments in which the present teachings may be practiced. The following description is, therefore, merely exemplary.

Disclosed herein is a sunscreen composition that provides protection to the skin against both the visible and UV portions of the sun's rays, as well as methods of using the sunscreen composition to reduce or prevent sunburn resulting from both the visible and UV portions of the sun's rays and methods of increasing the SPF and/or the visible light protection factor of a sunscreen composition. The sunscreen compositions disclosed herein comprise a combination of inorganic agents that absorb the sun's visible rays, primarily in the blue region, thereby reducing or preventing erythema.

In certain embodiments, disclosed herein is a sunscreen composition comprising at least one visible light protecting agent. Also disclosed herein is a sunscreen composition comprising at least two visible light protecting agents, such as barium sulfate and mica.

In certain embodiments, the sunscreen composition may further comprise iron oxide as an inorganic pigment, which also acts to absorb visible light, and in certain embodiments, the sunscreen composition may further comprise iron oxide together with at least one inorganic UV filtering agent, such as titanium dioxide and/or zinc oxide.

In certain embodiments, the sunscreen composition disclosed herein is anhydrous, and in certain embodiments, the sunscreen composition is in the form of an emulsion, such as an oil-in-water emulsion or a water-in-oil emulsion. The anhydrous sunscreen composition disclosed herein may provide superior water endurance properties when applied topically to a user's skin as compared to a water-based sunscreen composition, and in certain embodiments, the anhydrous sunscreen composition may be water-resistant. Additionally, the anhydrous sunscreen composition may provide enhanced resistance to microbial contamination as compared to a water-based sunscreen composition. In certain embodiments, the anhydrous sunscreen composition disclosed herein is substantially free of preservatives.

The sunscreen compositions disclosed herein provide superior protection against erythema caused by sunlight as compared to conventional sunscreen products, including, for example, conventional sunscreens that do not provide a combination of visible light blocking agents. The at least two visible light protecting agents such as barium sulfate and mica provide visible light protection that is synergistic and superior not only to iron oxide alone, but also to either visible light protecting agent alone, thereby allowing for the sunscreen composition to provide equivalent or superior visible light protection while containing a reduced amount of iron oxide, which may be undesirable as a pigment in tinted sunscreens for fair-skinned individuals. Accordingly, the sunscreen compositions disclosed herein provide visible light protection in a manner that is cosmetically-acceptable and can be adapted by concentration (e.g., the concentration of the iron oxide) and color grades to match the skin tone of the user.

The sunscreen compositions disclosed herein may be formulated to provide a physical feel and touch characteristics to be pleasant to the user. In certain embodiments, the sunscreen is formulated to provide an acceptable color match to an individual, such as an individual having Fitzpatrick Type I or Type II skin. In certain embodiments, the sunscreen is formulated to provide an acceptable color match to an individual having Fitzpatrick Type III, Type IV, Type V, or Type VI skin.

Definitions

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. The following terms and cognates thereof shall have the following meanings unless the context clearly indicates otherwise.

The term "at least one of" is used to mean one or more of the listed items can be selected. For example, if the listing of items is A and B, at least one of A and B indicates A alone, B alone, or A and B.

The term "about" is understood as encompassing a range of normal variation as accepted in the art and can include, for example, within 10%, 1%, 0.1% or 0.01% of the stated value. Unless otherwise indicated, all numerical values provided herein are understood as being modified by the term about.

As used herein, the term "erythema" is used interchangeably with the term "sunburn" and indicates a superficial reddening of the skin caused by overexposure to waves from the electromagnetic spectrum, including both visible light and UV radiation. As used herein, erythema and sunburn are distinguished from increased skin pigmentation (e.g., tanning).

As used herein, the term "ultraviolet radiation" or "UV radiation" indicates electromagnetic radiation in the range of about 290 nm to about 400 nm. Within the spectrum of UV radiation, UVB radiation is electromagnetic radiation within the range of about 290 nm to about 320 nm, while UVA radiation is electromagnetic radiation within the range of about 320 to about 400 nm.

As used herein, the term "visible light" indicates electromagnetic radiation in the range of about 400 nm to about 700 nm. Within the visible light spectrum, the violet light region spans about 380-450 nm, the blue light region spans about 450-495 nm, the green light region spans about 495-570 nm, the yellow light region spans about 570-590 nm, the orange light region spans about 590-625 nm, and the red light region spans about 625-700 nm. In certain embodiments, the blue light region may be combined with the violet light region to describe a blue light region that spans from about 400 nm to about 500 nm.

As used herein, the terms "sun protection factor" and "SPF" indicate a measure of how much solar energy is required to produce erythema, or sunburn, on skin after the application of a sunscreen composition relative to the amount of solar energy required to produce erythema on skin that does not have any sunscreen composition applied thereto. The amount of solar energy may be affected by both length (time) of exposure and intensity of the solar energy. Solar intensity may be related to time of day, geographic location (wherein a higher latitude may increase solar intensity), and weather (e.g., cloud coverage).

As used herein, the terms "visible light protection factor" or "VL-PF" indicate a measure of the effectiveness of a sunscreen composition to prevent the effect of erythema, or sunburn, caused by solar visible light after application of the sunscreen composition relative to the amount of solar energy required to produce erythema on skin that does not have any sunscreen composition applied thereto. In certain embodiments, the VL-PF corresponds to the inverse of the average transmission value across a given wavelength range, e.g., about 400 nm to about 800 nm, about 400 nm to about 600 nm, or about 400 nm to about 500 nm.

As used herein, the term "effective amount" refers to an amount of a sunscreen composition which, when applied or administered in an appropriate quantity and frequency, is sufficient to prevent, reduce, or mitigate the damage incurred from exposure to ultraviolet radiation and visible light, including sunburn.

Additional definitions are set forth throughout the detailed description.

Sunscreen Compositions

Disclosed herein are sunscreen compositions useful for reducing or preventing damage caused by visible light and UV radiation, including sunburn, when applied topically to a user's skin.

In certain embodiments there is disclosed a sunscreen composition comprising (a) at least one inorganic UV filtering agent, such as titanium oxide and/or zinc oxide; (b) at least one inorganic pigment selected from iron oxide; and (c) at least one visible light protecting agent, wherein the at least one visible light protecting agent is present in an amount effective to reduce or prevent sunburn caused from visible light. In certain embodiments there is disclosed a sunscreen composition comprising (a) at least one inorganic UV filtering agent, such as titanium oxide and/or zinc oxide; (b) at least one inorganic pigment selected from iron oxide; and (c) at least two visible light protecting agents comprising or consisting of barium sulfate and mica, wherein the at least two visible light protecting agents are present in an amount effective to reduce or prevent sunburn caused from visible light.

UV Filtering Agents

In certain embodiments, the sunscreen composition comprises at least one inorganic UV filtering agent selected from the group consisting of titanium dioxide, zinc oxide, cerium oxides, zirconium oxides, and mixtures thereof. Inorganic UV filtering agents may serve to filter, or absorb, UV radiation from the UV band of the electromagnetic spectrum, including, for example, UVA and UVB radiation at approximately 320-400 nm and 280-320 nm, respectively.

In certain embodiments, the sunscreen compositions disclosed herein may comprise titanium dioxide as an inorganic UV filtering agent. Titanium dioxide may be present as a solid particle that is micronized or nanosized, for example having a mean particle size ranging from about 10 nm to about 100 µm, such as from about 10 nm to about 25 µm, from about 10 nm to about 10 µm, or from about 15 nm to about 5 µm. In certain embodiments where titanium dioxide is present as a UV filtering agent, the titanium dioxide may comprise nanoparticles having a mean particle size ranging from about 5 nm to about 1000 nm, such as from about 5 nm to about 500 nm, from about 10 nm to 50 nm, or from about 15 nm to about 40 nm, or about 15 nm. Titanium dioxide nanoparticles may also form agglomerates having a larger mean particle size, such as, for example, a mean agglomerate particle size ranging from about 100 nm to about 1000 nm, such as, for example, about 200 nm to about 500 nm, or about 250 nm to about 400 nm. In certain embodiments, the titanium dioxide may be larger than nanoparticle-sized, having a mean particle size ranging from about 1 µm to about 25 µm, such as from about 5 µm to about 20 µm, or from about 10 µm to about 15 µm. In certain embodiments, the titanium dioxide comprises a mixture of nanoparticles (e.g., for UV filtering protection) and particles of a larger, micronized size (e.g., for visible light scattering protection).

Titanium dioxide may be present in the sunscreen composition in any amount effective to filter UV rays so as to prevent or reduce the effects of sunburn when applied topically to a user, either alone or together with other components of the sunscreen. In embodiments, titanium dioxide may be present in the sunscreen composition in an amount ranging from about 1% to about 25%, such as from about 5% to about 20%, or from about 5% to about 15%, such as about 5%, about 6%, about 7%, about 8%, about 9%, about 10%, about 11%, about 12%, about 12.5%, about 13%, about 14%, or about 15%, by weight based on the total weight of the sunscreen composition.

In various embodiments of the disclosure, in addition to or instead of titanium dioxide, the sunscreen composition comprises zinc oxide as an inorganic UV filtering agent. As discussed above for titanium dioxide, the zinc oxide may be present as a solid particle that is micronized or nanosized, for example having a mean particle size ranging from about 10 nm to about 400 µm, such as from about 10 nm to about 25 µm, from about 10 nm to about 10 µm, or from about 15 nm to about 5 µm. As used herein, "nanosized" or "nanoparticles" indicates a particle size that is under about 1000 nm, such as from about 1 nm to about 1000 nm or from about 1 nm to about 100 nm, while "micronized" or "microsized" indicates a particle size that ranges from about 1 µm (i.e., about 1000 nm) to about 1000 µm. In embodiments where zinc oxide is present as a UV filtering agent, the zinc oxide may comprise nanoparticles having a mean particle size ranging from about 5 nm to about 1000 nm, such as from about 10 nm to about 1000 nm, from about 30 nm to about 200 nm, from about 40 nm to about 100 nm, from about 60 nm to about 80 nm, from about 10 nm to 50 nm, or from about 25 nm to about 40 nm, or about 80 nm. As discussed below, however, zinc oxide may also be present in the sunscreen compositions disclosed herein as at least one inorganic pigment in pigmentary sizes, indicating that the zinc oxide may be larger than nanoparticle-sized, having a mean particle size ranging from about 100 nm to about 1000 nm, such as about 200 nm to about 500 nm, or from about 1 µm to about 400 µm, such as from about 10 µm to about 100 µm, from about 2 µm to about 25 µm, from about 5 µm to about 20 µm, or from about 10 µm to about 15 µm. In certain embodiments, the zinc oxide comprises a mixture of nanoparticles (e.g., for UV filtering protection) and particles of a larger, micronized size (e.g., for visible light scattering protection).

Zinc oxide may be present in the sunscreen composition in any amount effective to filter UV rays so as to prevent or reduce the effects of sunburn when applied topically to a user, either alone or together with other components of the sunscreen. In certain embodiments, zinc oxide may be present in the sunscreen composition in an amount ranging from about 1% to about 25%, such as from about 5% to about 20%, or from about 5% to about 15%, such as about 5%, about 6%, about 7%, about 7.5%, about 8%, about 9%, about 10%, about 11%, about 12%, about 13%, or about 15%, by weight based on the total weight of the sunscreen composition.

In total, the inorganic UV filtering agents, including both zinc oxide and titanium dioxide, may be present in the sunscreen composition in an amount ranging from about 2% to about 50%, such as from about 5% to about 40%, from about 10% to about 30%, or from about 20% to about 25%, such as about 20%, about 21%, about 22%, about 23%, about 23.5%, about 24%, or about 25%, by weight based on the total weight of the sunscreen composition.

In certain embodiments, the sunscreen composition may be formulated for use on a use with a fair complexion, such as for use on a user with Fitzpatrick Type I or Type II skin. In such embodiments, the amount of titanium dioxide in the composition may be greater than the amount of zinc oxide in the composition. While not wishing to be bound by theory, it is believed that titanium oxide may make a greater contribution to SPF protection as compared to zinc oxide.

In certain embodiments, the at least one inorganic UV filtering agent may be a surface-treating inorganic UV filtering agent. Surface treating the at least one inorganic UV filtering agent may reduce or prevent photoreactivity of the agent and/or aid in mixing with other ingredients in the sunscreen composition. A surface-treated inorganic UV filtering agent indicates that the UV filtering agent has been surface-treated by any means, including chemical, electrical, and/or mechanical means. In certain embodiments, surface treating at least one inorganic UV filtering agent may enhance the water-resistance properties of the UV filtering agent and the sunscreen composition. In certain embodiments, all of the UV filtering agents present in the sunscreen composition are surface-treated, which may reduce potential photoreactivity of the UV filtering agent.

An inorganic UV filtering agent may be surface-treated by any surface-treating method or agent known in the art. In certain embodiments, the at least one inorganic UV filtering agent may comprise coated particles. The coating may comprise, for example, hydrophobic materials such as alkyl siloxanes (e.g., triethoxycaprylylsilane), organotitanates, halogenated phosphates (e.g., perfluoro alkyl phosphonates), halogenated organosilanes, modified amino acids (e.g., disodium stearoyl glutamate), silicones, or metal salts of fatty acids.

Exemplary embodiments of a surface-treated coated UV filtering agent may include, for example, coated zinc oxide, such as triethoxycaprylylsilane zinc oxide (e.g., Z-Cote® HP 1), and/or coated titanium dioxide, such as triethoxycaprylylsilane titanium dioxide (e.g., CM3K40T4 by Kobo products, Inc. and UV Cut $TiO_2$-41).

Inorganic Pigments

In various embodiments, the sunscreen compositions disclosed herein may further comprise at least one inorganic pigment, such as iron oxide. While not wishing to be bound by theory, it is believed that the inorganic pigment acts to absorb the sun's visible rays, such as visible light in the blue light region of the visible light spectrum (e.g., about 450 nm to about 495 nm) and the violet light region of the visible light spectrum (e.g., about 380 nm to about 450 nm), which may overlap with UVA radiation at the upper end range of the UVA spectrum (e.g., about 375 nm to about 400 nm). Exemplary inorganic pigments may include titanium dioxide; zinc oxide; iron oxides, including black iron oxide, brown iron oxide, red iron oxide, and yellow iron oxide; manganese violet; ultramarine blue; chromium oxide, chromium hydrate; ferric blue; and mixtures thereof. In certain embodiments, the at least one inorganic pigment comprises a mixture of iron oxides, such as a mixture of red, yellow, and black iron oxides. It is noted that titanium dioxide and zinc oxide have a band gap energy of about 3.3 eV and will stop absorbing at about 375-380 nm, instead scattering at wavelengths above that range. Iron oxides and other oxides have a band gap energy of only about 2.1-2.2 eV and may absorb as far as about 500-590 nm, scattering above that wavelength range.

In one embodiment, the at least one inorganic pigment comprises iron oxide, and in one embodiment, the at least one inorganic pigment comprises iron oxide and at least one of zinc oxide and titanium dioxide. While traditional nano-sized particles of inorganic UV filtering agents such as titanium dioxide and zinc oxide may serve to provide UVB protection against radiation in the range of from about 280 nm to about 320 nm, these agents often fail to provide adequate protection from erythema in the higher radiation wavelengths constituting UVA radiation, such as from about 315 nm to about 400 nm, including from about 375 nm to about 400 nm. As disclosed herein, however, the addition of at least one inorganic pigment such as iron oxide, titanium dioxide, and/or zinc oxide may provide enhanced protection against erythema from UVA radiation and/or visible light, including, for example protection from UVA radiation in the range of about 375 nm to about 400 nm and visible light in the range of from about 400 nm to about 750 nm.

In embodiments wherein the at least one inorganic pigment comprises titanium dioxide and/or zinc oxide, the titanium dioxide and/or zinc oxide may have a particle size that is larger than the titanium dioxide and/or zinc oxide that comprises the UV filtering agents. Smaller nanosized particles of titanium dioxide and/or zinc oxide are known to provide broad-spectrum UV filtering and absorbing properties, but have a reduced ability to scatter and reflect visible light, making them more transparent when applied to the skin in the form of a sunscreen composition. See, e.g., Yin, H. et al., *A comparative study of the physical and chemical properties of nano-sized ZnO particles from multiple batches of three commercial products*, J. NANOPART. RES. 2015; 17:1-19.

Accordingly, in certain embodiments wherein the sunscreen composition disclosed herein comprises UV filtering agents of nanoparticles of zinc oxide and/or nanoparticles of titanium dioxide, the sunscreen composition may further comprise at least one inorganic pigment selected from the group consisting of pigmentary-sized zinc oxide and pigmentary-sized titanium dioxide. By "pigmentary" or "pigmentary-sized," it is indicated that the mean particle size of the titanium dioxide and/or zinc oxide is larger than the aforementioned nanosized particles and is of a cosmetically-acceptable size for use as a pigment in the sunscreen composition. In certain embodiments, pigmentary-sized particles of zinc oxide may have a mean particle size ranging from at least about 100 nm to about 25 µm, such as from about 200 nm to about 10 µm, from about 200 nm to about 500 nm, or from about 5 µm to about 15 µm. In certain embodiments, pigmentary-sized particles of titanium dioxide may have a mean particle size ranging from at least about 100 nm to about 25 µm, such as from about 200 nm to about 10 µm, from about 200 nm to about 500 nm, from about 5 µm to about 15 µm, or from about 8 µm to about 10 µm.

The at least one inorganic pigment may be present in the sunscreen composition in any amount effective to absorb visible light, such as visible light from the blue and/or violet regions of the visible light spectrum, either alone or together with other components of the sunscreen composition. In certain embodiments, the at least one inorganic pigment such as iron oxide is present in the sunscreen composition in an amount ranging from about 0.01% to about 10% by weight, such as from about 1% to about 5%, from about 1% to about 4.5%, or from about 1% to about 3%, such as about 0.5%, about 1%, about 1.5%, about 2%, about 2.5%, or about 2.75%, by weight based on the total weight of the sunscreen composition. In certain embodiments, iron oxide is present in the sunscreen composition in an of less than 5%, such as less than about 4.5%, less than about 3%, less than about 2.75%, less than about 2.5%, less than about 2%, less than about 1.5%, less than about 1%, or less than about 0.5%, by weight based on the total weight of the sunscreen composition. In some embodiments, the composition is substantially free of iron oxide. According, also disclosed herein a sunscreen composition at least one inorganic UV filtering agent selected from zinc oxide or titanium dioxide; and at least two visible light protecting agents comprising barium sulfate and mica, wherein the at least two visible light protecting agents are present in an amount effective to reduce or prevent sunburn caused from visible light.

In certain embodiments, the at least one inorganic pigment may be a surface-treated inorganic pigment. Surface treating the at least one inorganic pigment may reduce or prevent photoreactivity of the pigment and/or aid in mixing with other ingredients in the sunscreen composition. A surface-treated inorganic pigment indicates that the inorganic pigment has been surface-treated by any means, including chemical, electrical, and/or mechanical means. In certain embodiments, surface treating the at least one inorganic pigment may enhance the water-resistance properties of the inorganic pigment and the sunscreen composition. In certain embodiments, all of the inorganic pigments present in the sunscreen composition are surface-treated.

An inorganic pigment may be surface-treated by any surface-treating method or agent known in the art. In certain embodiments, the at least one inorganic pigment may comprise coated particles. The coating may comprise, for example, hydrophobic materials such as alkyl siloxanes (e.g., triethoxycaprylylsilane), organotitanates, halogenated phosphates (e.g., perfluoroalkyl phosphonates), halogenated organosilanes, modified amino acids (e.g., disodium stearoyl glutamate), silicones, or metal salts of fatty acids.

Exemplary embodiments of in organic pigments may include surface-treated coated inorganic pigments such as coated iron oxides, including triethoxycaprylylsilane iron oxides (e.g., Unipure®) and coated and uncoated titanium dioxides (e.g., Unipure® White LC 987 and Unipure® White LC 987 AS-EM, a triethoxycaprylylsilane titanium dioxide).

Additional Visible Light Protecting Agents

In certain embodiments, the sunscreen compositions disclosed herein comprise, in addition to the at least one inorganic pigment, further comprise at least one visible light protecting agent, such as barium sulfate. In certain embodiments, the sunscreen composition further comprises at least two additional visible light protecting agents, such as barium sulfate and mica. Visible light protecting agents may comprise any compound, such as inorganic pigments, that block or absorb light from the visible light portion of the electromagnetic spectrum, e.g., electromagnetic wavelengths in the range of about 400 nm to about 700 nm. In certain embodiments, the visible light protecting agent blocks or absorbs light from the violet and/or blue light region, e.g., from about 380 nm to about 500 nm, from about 400 nm to about 495 nm, or from about 400 nm to about 500 nm. In certain embodiments, the visible light protecting agent blocks or absorbs light from the violet light region, e.g., from about 380 nm to about 450 nm, and in certain embodiments, the light absorbing agent blocks or absorbs light from the blue light region, e.g., from about 450 nm to about 495 nm. In certain embodiments, the visible light protecting agent blocks or absorbs light from the green light region, e.g., from about 495 nm to about 570 nm; the yellow light region, e.g., from about 570 nm to about 590 nm; the orange light region, e.g., from about 590 nm to about 625 nm; and/or the red light region, e.g., from about 625 nm to about 700 nm.

Visible light protecting agents may include, by way of non-limiting examples, at least one or at least two of transition metal oxides, iron oxides, barium sulfate, mica, silica, bismuth oxychloride, corn starch, calc powder, or any visible colored pigment known in the art. In certain embodiments, the at least one visible light protection agent is barium sulfate. In certain embodiments, the at least one visible light protecting agent is mica. In certain embodiments, the at least two visible light protecting agents are barium sulfate and mica. In certain embodiments, the sunscreen composition is substantially free of bismuth oxychloride. In certain embodiments, the sunscreen composition is substantially free of any visible light protecting agent other than barium sulfate and/or mica.

The at least one or at least two visible light protecting agents may be present in the sunscreen composition in any amount effective to absorb visible light, such as visible light from the blue and/or violet regions of the visible light spectrum, either alone or together with other components of the sunscreen composition, e.g., iron oxide, titanium oxide, and or zinc oxide.

In embodiments disclosed herein, the at least two visible light protecting agents may be present together in a synergistic amount, such that the presence of the at least two visible light protecting agents is capable of blocking a greater amount of visible light than either visible light protecting agent acting alone. For example, barium sulfate and mica may be present in the sunscreen composition is a synergistic amount. In certain embodiments, the at least one or the at least two visible light protecting agent or agents may be present in the sunscreen composition in an amount that is synergistic with another component of the sunscreen composition, such as, for example, at least one antioxidant.

As used herein, the terms "synergy," "synergistically," and derivations thereof, indicate that the activity of the combination, such as the combination of the at least two visible light protecting agents, is greater than the sum of the visible light protecting agents when applied individually. In some embodiments, each individual visible light protecting agent may have minimal visible light protecting effect when applied separately; however, the same amount of the visible light protecting agents, when applied together in combination in a sunscreen composition, may have a high visible light protecting capability, resulting in a higher SPF and/or visible light protection factor. This synergy of the at least two visible light protecting agents is surprising and unexpected.

In certain embodiments, the at least one visible light protecting agent, such as barium sulfate, is present in the sunscreen composition in an amount ranging from about 0.01% to about 10% by weight such as from about 1% to about 7%, from about 1% to about 5%, or about 5%, by weight based on the total weight of the sunscreen composition.

In certain embodiments, the at least two visible light protecting agents such as barium sulfate and mica are present in the sunscreen composition together in an amount ranging from about 0.01% to about 10% by weight, such as from about 1% to about 7%, from about 1% to about 5%, or about 5%, by weight based on the total weight of the sunscreen composition. In certain embodiments, at least two visible light protecting agents such as barium sulfate and mica are present in the sunscreen composition together in an amount from about 0.01% to less than about 7% by weight, such as from about 3.5% to less than about 7%, from about 4% to less than about 7%, from about 4.5% to less than about 7%, or from about 5% to less than about 7%, by weight based on the total weight of the sunscreen composition. The amount of barium sulfate and mica in the composition may be the same or different.

In certain embodiments of the sunscreen compositions disclosed herein, barium sulfate is present in an amount ranging from about 0.01% to about 5%, such as from about 1% to about 3.5%, from about 1% to about 3%, from about 1.5% to about 2.5%, from about 2% to about 2.5%, or about 2.5%, by weight based on the total weight of the sunscreen composition. In certain embodiments of the sunscreen compositions disclosed herein, mica is present in an amount ranging from about 0.01% to about 5%, such as from about 1% to about 3.5%, from about 1% to about 3%, from about 1.5% to about 2.5%, from about 2% to about 2.5%, or about 2.5%, by weight based on the total weight of the sunscreen composition. In certain embodiments disclosed herein, both barium sulfate and mica are each present in the sunscreen composition in an equal amount, such as, for example, each from about 1% to about 3%, from about 1.5% to about 2.5%, from about 2% to about 2.5%, or about 2.5%, by weight based on the total weight of the sunscreen by weight based on the total weight of the sunscreen composition. In one embodiment disclosed herein, the sunscreen composition comprises at least two visible light protecting agents comprising barium sulfate and mica, wherein the barium sulfate is present in an amount of about 2.5% and the mica is present in an amount of about 2.5%, by weight based on the total weight of the sunscreen composition.

In certain embodiments disclosed herein, at least one of the at least two visible light protecting agents may be a surface-treating visible light protecting agent. Surface treating the at least one visible light protecting agent may reduce or prevent photoreactivity of the agent and/or aid in mixing with other ingredients in the sunscreen composition. A surface-treated visible light protecting agent indicates that the visible light protecting agent has been surface-treated by any means, including chemical, electrical, and/or mechanical means. In certain embodiments, surface treating the at least one visible light protecting agent may enhance the water-resistance properties of the visible light protecting agent and the sunscreen composition. In certain embodiments, both of the at least two visible light protecting agents (e.g., both barium sulfate and mica) present in the sunscreen composition are surface-treated, and in certain embodiments, only one of the at least two visible light protecting agents (e.g., either barium sulfate or mica) present in the sunscreen composition is surface-treated.

A visible light protecting agent may be surface-treated by any surface-treating method or agent known in the art. In certain embodiments, the at least one visible light protecting agent may comprise coated particles. The coating may comprise, for example, hydrophobic materials such as alkyl siloxanes (e.g., triethoxycaprylylsilane), organotitanates, halogenated phosphates (e.g., perfluoro alkyl phosphonates), halogenated organosilanes, modified amino acids (e.g., disodium stearoyl glutamate), silicones, or metal salts of fatty acids.

Exemplary embodiments of a surface-treated coated visible light protecting agent may include, for example, coated barium sulfate, such as triethoxycaprylylsilane barium sulfate, and/or coated mica, such as triethoxycaprylylsilane mica.

Additional Ingredients

The sunscreen compositions of the present disclosure may comprise any other additional ingredients known in the art to be cosmetically acceptable for use in a topical sunscreen product. For example, in certain embodiments, the sunscreen compositions disclosed herein may further comprise at least one of antioxidants, emollients/oils, emulsifiers, SPF boosters, organic pigments, organic UV filtering agents, skin conditioning agents, film formers, fillers, preservatives, fragrances, silica, sodium chloride, citric acid, neutralizing or pH-adjusting agents (e.g., triethanolamine and sodium hydroxide), essential oils, and cosmetically-acceptable carriers, including water. In certain embodiments, the sunscreen composition disclosed herein is substantially free of water and is an anhydrous sunscreen composition.

In certain embodiments disclosed herein, the sunscreen composition further comprises at least one antioxidant. While not wishing to be bound by theory, it is believed that the at least one antioxidant helps to quench free radicals induced by the sun's visible light radiation, thereby effectively preventing or reducing sunburn when applied topically to a user in an amount effective to quench free radicals. In certain embodiments, the at least one antioxidant may be selected from vitamin A, vitamin C, vitamin E, selenium, carotenoids (e.g., beta-carotene), thiols, and derivatives and mixtures thereof. In certain embodiments, the at least one antioxidant is vitamin E (e.g., tocopherol) or a derivative thereof, such as tocopherol acetate. In certain embodiments, the at least one antioxidant is vitamin C (e.g., ascorbic acid) or a derivative thereof, such as tetrahexyldecyl ascorbate. In certain aspects of the disclosure, the at least one antioxidant comprises both vitamin E or a derivative thereof and vitamin C or a derivative thereof.

The at least one antioxidant may be present in the sunscreen compositions disclosed herein in any amount effective to prevent or reduce sunburn caused from the visible light region of the electromagnetic spectrum (e.g., about 400-750 nm), either alone or together with other components of the sunscreen composition. In certain embodiments, vitamin C or a derivative thereof, such as tetrahexyldecyl ascorbate, is present in the sunscreen composition in an amount ranging from about 0.01% to about 5%, such as from about 0.1% to about 3%, from about 0.2% to about 2%, or from about 0.2% to about 1%, by weight relative to the total weight of the sunscreen composition. In certain embodiments, vitamin E or a derivative thereof, such as tocopherol acetate, is present in the in the sunscreen composition in an amount ranging from about 0.01% to about 5%, such as from about 0.1% to about 3%, from about 0.2% to about 2%, or from about 0.2% to about 1%, by weight relative to the total weight of the sunscreen composition. In certain embodiments, the at least one antioxidant is a combination of vitamin C or a derivative thereof and vitamin E or a derivative thereof, and is present in the sunscreen composition in an amount ranging from about 0.1% to about 10%, such as from about 0.2% to about 5%, from about 0.5% to about 4%, or from about 0.4% to about 2%, by weight relative to the total weight of the sunscreen composition.

In certain embodiments, the sunscreen composition further comprises at least one organic UV filtering agent, and in certain embodiments, the sunscreen composition does not comprise an organic UV filtering agent, such that the only UV filtering agents in the sunscreen composition are inorganic UV filtering agents. Traditional organic UV filtering agents are small, aromatic molecules, although any organic UV filtering agent known in the art may be considered within the scope of embodiments disclosed herein. For example, the at least one organic UV filtering agent disclosed herein may be selected from benzophenones (such as benzophenone-3, benzophenone-5, and benzophenone-8), 3-benzylidene camphor, bis ethylhexyloxyphenol methoxyphenyl triazine, butylmethoxy dibenzoyl methane, camphor benzalkonium methosulfate, diethylamino hydroxybenzoyl hexyl benzoate, diethylhexyl butamido triazone, drometrizole trisiloxane, ethoxyethyl methoxycinnamate, ethylhexyl dimethylamino benzoate, ethylhexyl methoxycinnamate, ethylhexyl salicylate, ethylhexyl triazone, homosalate, isoamyl p-methoxycinnamate, methyl anthranilate, 4-methylbenzylidene camphor, methylene bis-benzotriazolyl tetramethylbutylphenol, octocrylene, para aminobenzoic acid (PAB A), polyacrylamide methylbenzylidene camphor, polysilicone-15, triethanolamine salicylate, and terephtalydene dicamphor sulfonic acid.

In certain embodiments, the sunscreen composition further comprises at least one humectant, such as, for example, butylene glycol or glycerin.

In certain embodiments, the sunscreen composition may comprise at least one emollient. Suitable emollients may be chosen from any emollient known in the art, including, for example, mineral oils, petroleum, vegetable/plant oils such as triglycerides (e.g., caprylic/capric triglycerides), waxes (e.g., beeswax), isopropyl palmitate, isopropyl myristate, diisopropyl adipate, dibutyl adipate, butyloctyl salicylate, C12-C15 alkyl benzoates, silicone oils (e.g., dimethicone and stearyl dimethicone), animal oils, hydrocarbon oils, and fatty acids. By way of example, the at least one emollient may be chosen from alkane oils such as isododecane and isohexadecane, ester oils, ether oils (e.g., dicaprylyl ether), and artificial triglycerides (e.g., capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), glyceryl tri(caprate/caprylate/linolenate, and mixtures thereof).

Exemplary ester oils may include, for example, ethyl palmitate; ethylhexyl palmitate; isopropyl palmitate; dicaprylyl carbonate; alkyl myristates such as isopropyl myristate and ethyl myristate; isocetyl stearate; 2-ethylhexyl isononanoate; isononyl isononanoate; isodecyl neopentanoate; isostearyl neopentanoate; diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis (2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate; diisopropyl adipate; dioctyl adipate; 2-ethylhexyl hexanoate; ethyl laurate; cetyl octanoate; octyldodecyl octanoate; myristyl propionate; 2-ethylhexyl 2-ethylhexanoate; 2-ethylhexyl octanoate; 2-ethylhexyl caprylate/caprate; methyl palmitate; isononyl isononanoate; isohexyl laurate; hexyl laurate; isopropyl isostearate; isodecyl oleate; glyceryl tri (2-ethylhexanoate); pentaerythrithyl tetra(2-ethylhexanoate); 2-ethylhexyl succinate; C10-30 cholesterol/lanosterol esters; and mixtures thereof.

In certain embodiments, the sunscreen composition may further comprise at least one SPF booster. An SPF booster is a compound that acts to refract UV radiation, thereby increasing the pathlength of the light within the media and providing more UV absorption interactions with UV filtering agents, when both compounds are together. For example, in certain embodiments, styrene copolymer "spheres" can also be used to scatter UV and visible light radiation through this mechanism. The at least one SPF booster may be chosen from any SPF boosters known in the art, including, for example, diethylhexyl syringylidenemalonate; glass microspheres such as calcium aluminum borosilicate, sodium borosilicate, and calcium/sodium borosilicate; and copolymers of styrene and (meth)acrylic acid.

In certain embodiments, the sunscreen composition may further comprise at least one preservative. Suitable preservatives may include, but are not limited to, chlorophenesin, sorbic acid, disodium ethylenedinitrilotetraacetate, ethylhexylglycerin, phenoxyethanol, methylparaben, ethylparaben, propylparaben, phytic acid, imidazolidinyl urea, sodium dehydroacetate, benzyl alcohol, sodium benzoate, methylchloroisothiazolinone, methylisothiazolinone, and mixtures thereof.

In certain embodiments, the sunscreen composition may further comprise at least one skin-conditioning agent, which, in certain embodiments, may also function as a film former and/or emulsifier. Suitable skin conditioning agents may include, but are not limited to, glycerins, such as ethoxylated glycerine and propoxylated glycerine; sugar alcohols such as propylene glycol, dipropylene glycol, butylene glycol, hexylene glycol, pentylene glycol, polypropylene glycol, polyethylene glycol, caprylyl glycol, sorbitol, hydroxypropyl sorbitol, erythritol, threitol, pentaerythritol, xylitol, glucitol, and mannitol; hexane triol (e.g., 1,2,6-hexanetriol); glyceryl stearate; dimethicone; cyclomethicone; phenyl trimethicone; phenyl dimethicone; cetyl dimethicone; stearyl dimethicone; caprylyl methicone; amodimethicone; C30-45 alkyl dimethicones and methicones; cetearyl methicone; dimethicone copolyol; cyclopentasiloxane (such as Bentone Gel®); dimethicone crosspolymers; dimethicone/vinyl dimethicone crosspolymers; C30-45 alkyl cetearyl dimethicone crosspolymers; cetearyl dimethicone crosspolymers; dimethicone/phenyl vinyl dimethicone crosspolymer; vinyl dimethicone/lauryl dimethicone crosspolymer; trifluoropropyl dimethicone/trifluoropropyl divinyldimethicone crosspolymer; trimethylsiloxysilicate; trisiloxane; neopentyl glycol diheptanoate; neopentyl glycol diethylhexanoate; neopentyl glycol dicaprylate/dicaprate; neopentyl glycol diglycidyl ether; neopentyl glycol dicaprate; neopentyl glycol diisostearate; butyloctyl salicylate; ethylhexyl stearate; diethylhexyl 2,6-naphthalate; petrolatum; beeswax; shea butter; shea butter oil; cocoa butter; jojoba butter; aloe butter; olive butter; coconut oil; jojoba oil; olive oil; sunflower seed oil; and mixtures thereof.

In certain embodiments, the sunscreen composition may further comprise at least one film former. Suitable film formers may include, but are not limited to, polyurethanes, acrylates/dimethicone crosspolymer, waxes, silicone acrylates, and mixtures thereof.

The sunscreen compositions disclosed herein may be prepared by any means known in the art, such as mixing and blending the ingredients of the composition in any manner acceptable in the art. In certain embodiments, the sunscreen composition may be prepared by combining ingredients into a commercially-available topical carrier, which may comprises other ingredients dissolved or dispersed therein, such as film formers, surfactants, emulsifiers, thickeners, emollients, preservatives, pH adjusters, colorants, and fragrances, for example.

Methods of Using Sunscreen Compositions

Also disclosed herein are methods of reducing or preventing sunburn. The methods disclosed herein may comprise topically applying an effective amount of a sunscreen composition as disclosed herein to a surface of the user's body, such as, for example, the hair, skin, nails, or lips. As used herein, an effective amount can be any amount that reduces or prevents sunburn from exposure to both UV radiation and visible light. In certain embodiments, an effective amount may range, for example, from about 0.5 $mg/cm^2$ to about 5 $mg/cm^2$, such as from about 1 $mg/cm^2$ to about 3 $mg/cm^2$, or about 2 $mg/cm^2$. In certain embodiments, the methods disclosed herein further comprise allowing the sunscreen composition to dry after application. In certain embodiments, the sunscreen may be allowed to dry for a time period ranging from about 5 minutes to about 30 minutes, such as about 10 minutes, about 15 minutes, about 20 minutes, or about 25 minutes.

By topically applying the sunscreen composition, it is understood to mean that the sunscreen composition may be applied to any surface of the user, including, for example, the skin, hair, nails, and/or lips. The sunscreen composition may be topically applied in any manner known in the art, including by spray application, wiping, laying, spreading, or rubbing with hands or with an applicator, such as a spray bottle, wipe, roller, etc.

The effectiveness of a sunscreen's ability to block UV and/or visible light may be evaluated by any means known in the art. In certain embodiments, spectrophotometric measurements such as thin film spectrophotometry may be used. See, e.g., Cole, C. et al., *Evaluating sunscreen ultraviolet protection using a polychromatic diffuse reflectance device*, PHOTODERMATOLOGY, PHOTOIMMUNOLOGY, & PHOTOMEDICINE 2019, 25(6):436-441. In certain embodiments, a sunscreen may be evaluated by the Food and Drug Administration (FDA) Critical Wavelength test as set forth in the FDA Sunscreen Monograph: Labeling and Effectiveness Testing: Sunscreen Drug Products for Over-the-Counter Human Use. Federal Register 2011, 76:117, 35661-35665), and in certain embodiments, the ISO24443 in vitro UVA protection standard as set forth in the ISO24442 Determination of sunscreen UVA protection in vitro, 2021, may be used. In certain embodiments, a spectroradiometer may be used for spectral scans of the sunscreen using an illumination source, such as, for example, a solar simulator. The irradiance of the solar simulator may then be measured across a spectra of the electromagnetic radiation spectrum, e.g., from 290 nm to 800 nm, to arrive at a spectrophotometric measurement.

In certain embodiments, Hybrid Diffuse Reflectance Spectroscopy (HDRS) may be used to calculate the absorbance of a sunscreen formulation. HDRS may be used to provide measurements of the protection provided in the UVA portion of the electromagnetic radiation spectrum on human skin. For example, HDRS measurements of a formulation on human skin can be used to scale in vitro data to an appropriate amplitude by matching a calculated UVA protection factor (UVA-PF) of the in vitro spectra to UVA-PF values measured by HDRS. In certain embodiments, visible light blocking protection factors, which are analogous to SPF values but without biological weighting, may be calculated by determining the inverse of an average transmission value across a given wavelength range.

Disclosed herein are methods of increasing a visible light protection factor (VL-PF) of a sunscreen composition comprising at least one inorganic UV filtering agent and at least one inorganic pigment selected from iron oxide, the method comprising adding to the sunscreen composition at least one or at least two additional visible light protecting agents, such as at least two visible light protecting agents comprising barium sulfate and mica, wherein the at least one or at least two additional visible light protecting agents are present in an amount effective to increase the visible light protection factor of the sunscreen composition. The VL-PF is analogous to SPF values as described herein, but without a biological weighting. The VL-PF may be calculated by any means known in the art. For example, in certain embodiments, the VL-PF may be calculated by determining the inverse of the average transmission value across a given wavelength range, for example using the formula:

$$VL-PF = \frac{1}{10^{-\left(\sum_{nm_1}^{nm_2} A\right)/(nm_2-nm_1)}}$$

In various aspects of the disclosure, the VL-PF of the sunscreen compositions disclosed herein may be increased over a wavelength range spanning about 400-800 nm, such as about 400-600 nm or about 400-500 nm, by an amount of at least about 0.1, such as, for example, at least about 0.2, at least about 0.3, at least about 0.4, at least about 0.5, at least about 0.6, at least about 0.7, at least about 0.8, at least about 0.9, or at least about 1.0. In certain embodiments, the VL-PF of the sunscreen compositions disclosed herein may range from about 1 to about 5, such as, for example, about 1, about 1.5, about 2, about 2.5, about 3, about 3.5, about 4, about 4.5, or about 5.

Also disclosed herein are methods of increasing the SPF of a sunscreen composition, the method comprising adding at least one inorganic UV filtering agent; at least one inorganic pigment selected from iron oxide, and at least one or at least two visible light protecting agents, such as barium sulfate and mica, to a sunscreen composition. SPF, or sun protection factor, may be measured by any means known in the art and as described herein. In one embodiment, SPF may be measured by the protocol set forth by the International Organization for Standardization (ISO) 24444:2019, which measures SPF in an indoor laboratory in terms of the ratio of [the amount of UV radiation required to produce erythema on sunscreen-protected skin] to [the amount of UV radiation required to produce erythema on sunscreen-unprotected skin]. As the standard set forth in ISO 24444:2019 defines SPF in terms of UV radiation (i.e., under 400 nm), it does not consider, and in fact excludes, the effects of real-life solar exposure, including the effects of visible light. Indeed, laboratory-based SPF testing typically uses solar stimulators that emit UV radiation only in the 290-400 nm region of the spectrum, while adding filters to eliminate radiation below 290 nm and above 400 nm, and significantly diminish the content between 380 and 400 nm. Accordingly, the effects of long wavelength UVA and visible light on skin are not taken into account in many SPF determinations, including indoor laboratory-based SPF determinations that are used for many commercially-available sunscreen products.

In various aspects of the methods disclosed herein, SPF is determined based on actual outdoor solar exposure and may be defined in terms of the ratio of [the least amount of solar exposure required to produce erythema on sunscreen-protected skin] to [the amount of solar exposure required to produce erythema on sunscreen-unprotected skin]. Thus, SPF as used herein accounts for all of the effects from actual outdoor solar exposure, including both UV radiation and visible light and represent the performance of the product under actual use conditions.

In various aspects of the disclosure, the SPF of the sunscreens disclosed herein may be increased by an SPF of at least about 3, such as at least about 4, at least about 5, or at least about 6, as compared to a sunscreen composition that does not contain an effective amount of at least one or at least two visible light protecting agents, when tested under outdoor solar exposure conditions. In certain aspects, the SPF of the sunscreens disclosed herein may be increased by an SPF ranging from about 2 to about 10, such as from about 3 to about 5, or from about 3 to about 4, when tested under outdoor solar exposure conditions. While this level of increase may appear small relative to SPF claims generated with indoor solar simulator test methods, it is in fact proportionally much higher in impact when comparing products tested in outdoor conditions, where the maximum observed SPF values for SPF 60-100 claiming sunscreens is in the 8 to 10 range. See, e.g., Hughes SNG, Lowe NJ, Gross K, Mark L, Goffe B, Hughes H, Cole C. Assessment of Natural Sunlight Protection Provided by 10 High SPF Broad Spectrum Sunscreens and Sun Protective Fabrics. Curr Probl Dermatol. 2021; 55. in press. DOI: 10.1159/000517666. Thus an increase of 2-6 SPF units above this 8 to 10 maximal observed results in outdoor use conditions represent a significant boost in real protection.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with" or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

EXAMPLES

Example 1

Five anhydrous sunscreen stick compositions (0322A, 0211A, 0211B, 0211D, and 0314A) and one cream formulation (137-1216A) were prepared for evaluation and were formulated as shown below in Table 1.

TABLE 1

Sunscreen formulations

| | 0322A Control | 0211A (+Barium Sulfate) | 0211B (+Silica) | 0211D (+Bismuth oxychloride and mica) | 0314A (+Mica) | 137-1216A Visible Light Sunscreen |
|---|---|---|---|---|---|---|
| Titanium Dioxide (75% nano, 25% micron) | 23.5% | 23.5% | 23.5% | 23.5% | 23.5% | 12.0% |
| Zinc Oxide | — | — | — | — | — | 10.8% |
| Iron Oxide | 2.75% | 2.75% | 2.75% | 2.75% | 2.75% | 4.5% |
| Barium Sulfate | — | 5.0% | — | — | — | — |
| Silica | — | — | 5.0% | — | — | — |
| Bismuth Oxychloride | — | — | — | 3.9% | — | — |
| Mica | — | — | — | 4.4% | 5.0% | — |

All of the formulations listed above in Table 1 further comprised C12-15 alkyl benzoate, beeswax, butyloctyl salicylate, copernica cerifa (carnauba) wax, aluminum hydroxide or alumina, tocopheryl acetate, and triethoxycapryilsilane. The control formulation #0322 as well as formulations 0211A, 0211B, 0211D, and 0314A were anhydrous stick base compositions that additionally comprised isohexadecane, caprylic/capric triglyceride, shea butter, triacontanyl PVP, and stearic acid. The formulations 137-1216A was a cream base formulation that additionally comprised cyclopentasiloxane, ethylhexyl methoxycrylene, trimethylsiloxysilicate, PEG-10 dimethicone, silica cetyl silylate, distearimonium hectorite, tetrahexyldecyl ascorbate, C10-30 cholesterol/lanosterol esters, propylene carbonate, hydrogen dimethicone, phenoxyethanol, and fragrance.

The sunscreen stick and cream formulations containing inorganic sunblock filters and visible light blocking additives were evaluated for their ability to protect against both UV and visible light radiation.

In vitro UV and visible spectrophotometric assessment from 290-800 nm: The UV and visible light absorption spectrum of the sunscreen formulations in Table 1 were evaluated in vitro using conventional thin film spectrophotometry similar to that used for the Food and Drug Administration (FDA) Critical Wavelength test (FDA Sunscreen Monograph: Labeling and Effectiveness Testing: Sunscreen Drug Products for Over-the-Counter Human Use. Federal Register 2011, 76:117, 35661-35665) and the ISO24443 in vitro UVA protection standard (ISO24442 Determination of sunscreen UVA protection in vitro, 2021).

Helioscreen HD6 polymethylmethacrylate (PMMA) plates were individually weighed and tared, smeared with a test sunscreen composition, and rubbed by finger to a uniform film, resulting in a total weight per unit area of 0.7 mg/cm$^1$. Sunscreen treated plates were prepared in duplicate. Three blank PMMA plates were prepared with glycerin application to be used as controls.

An Optronics® 756 spectroradiometer with a 6-inch integrating sphere entrance port was used for the spectral scans of the blank PMMA control plates, as well as each of the sunscreen treated plates. The illumination source was a Solar® Light LS1000 Solar Simulator with a 9-inch diameter beam. The irradiance of the solar simulator was measured from 290 nm to 800 nm, measuring the glycerin-treated control PMMA plates first by placing them over the input port of the spherical integrator entrance to the spectroradiometer. Next, each of the sunscreen treated plates was measured in the same manner and position.

The absorbance of the sunscreen compositions was calculated using the following equation: $A = -\log(I_{SS\ treated}/I_{blank})$, wherein A is absorbance, $I_{SS\ treated}$ is irradiance of the solar simulator with the sunscreen-treated plate over the entrance port, and blank is the irradiance of the solar simulator with the glycerin-treated control plate of the entrance port.

Hybrid Diffuse Reflectance Spectroscopy (HDRS): While the spectrophotometric measurements described above are appropriate for determining relative spectral shape or quality, the absolute amplitude of the absorbance curves may be susceptible to the uniformity of the spreading of the formulations on the PMMA plates, as well as the ability of the sunscreen to set up a uniform and contiguous film on the surface of the plates. Thus, those measurements may provide a less accurate estimate of the absolute amplitude of the absorbance curve recorded. This is also why in vitro thin film spectroscopic methods are typically not approved for assessment of the magnitude of sunscreen protection, and relative shape measurements, such as Critical Wavelength, may be used instead for labeling.

HDRS bridges this gap and provides measurements of the absolute protection provided in the UVA portion of the spectrum on human skin. HDRS measurements of the same formulation on human skin can then be used to scale the in vitro data to the appropriate amplitude by matching the calculated UVA protection factor (UVA-PF) of the in vitro spectra to the UVA-PF values measured by HDRS.

In this example, HDRS measurements of the UVA-PF values of the test formulations described in Table 1 were conducted using a Solar Light Polychromatic HDRS device. The device emits UVA light onto the skin, which is then scattered within the epidermis and dermis. A portion of that light is re-emitted from the skin and captured by light fibers in bundles on the device and measured with a photomultiplier tube. In the Examples set forth herein, this was done first without any sunscreen on the skin, and then again after sunscreen had been applied and dried for 15 minutes. The UVA-PF of the sunscreen formulation was calculated as using the following Formula 1:

$$UVA-PF = \sqrt{\frac{I_{no\ sunscreen}}{I_{sunscreen}}} \quad \text{Formula 1}$$

wherein $I_{no\ sunscreen}$ is the intensity of the remitted light without any sunscreen on the skin, and $I_{sunscreen}$ is the intensity of the remitted light with sunscreen applied to the skin. The square root function is used because the measured light intensity passes through the sunscreen film twice.

The UVA-PF of each formulation as measured by HDRS was calculated, as well as the UVA-PF of the in vitro spectra as described above. The in vitro spectral absorbance (290-800 nm) were multiplied by a single numerical factor "s" to scale the in vitro spectra to yield a UVA-PF value identical to the HDRS determined UVA-PF value. The results are shown in FIG. 1, wherein the control sunscreen 0332A (containing titanium oxide and 2.75% iron oxide, but no barium sulfate, silica, bismuth oxychloride, or mica) had the lowest absorbance spectra across the UV and visible light wavelengths. The mica-containing stick formulation had the highest visible light blocking absorbance, comparable to the visible sunscreen cream that contained 4.5% iron oxide. The mica-containing stick formulation had the highest visible light blocking absorbance for wavelengths above 525 nm, demonstrating an absorbance that was even higher than the visible sunscreen cream.

The Visible Light Protection Factor (VL-PF) was calculated by determining the inverse of the average transmission value across a given wavelength range. The following formula was used:

$$VL-PF = \frac{1}{10^{-\left(\sum_{nm_1}^{nm_2} A\right)/(nm_2-nm_1)}}$$

Table 2 below shows the VL-PFs calculated for each of the six tested formulations over the visible light spectra ranging from 400-500 nm, 400-600 nm, and 400-800 nm.

TABLE 2

| Visible Light Protection Factors | | | | | |
|---|---|---|---|---|---|
| | | | 0211D | | 137-1216A |
| | 0211A | | (+Bismuth | | Visible |
| 0322A | (+Barium | 0211B | oxychloride | 0314A | Light |
| Control | Sulfate) | (+Silica) | and mica) | (+Mica) | Sunscreen |
| 400-500 nm | 3.2 | 3.8 | 3.7 | 3.5 | 4.3 | 4.5 |
| 400-600 nm | 2.5 | 2.7 | 2.7 | 2.6 | 3.1 | 3.1 |
| 400-800 nm | 1.8 | 1.9 | 1.9 | 1.9 | 2.2 | 2.1 |

The values can also be calculated as a percent of visible light blocked by the sunscreen, using the following formula:

$$\%\ Blocked = \left(100 - \left(\frac{100}{VL_{PF}}\right)\right)\%,$$

wherein the results are shown below in Table 3.

TABLE 3

| Percent Visible Light Blocked | | | | | |
|---|---|---|---|---|---|
| | | | 0211D | | 137-1216A |
| | 0211A | | (+Bismuth | | Visible |
| 0322A | (+Barium | 0211B | oxychloride | 0314A | Light |
| Control | Sulfate) | (+Silica) | and mica) | (+Mica) | Sunscreen |
| 400-500 nm | 69.0% | 73.5% | 72.9% | 71.2% | 76.9% | 77.7% |
| 400-600 nm | 59.4% | 63.5% | 62.6% | 61.9% | 67.9% | 67.4% |
| 400-800 nm | 44.7% | 48.4% | 47.4% | 47.5% | 54.3% | 51.7% |

As shown in Tables 2 and 3 above, the mica additive to an iron oxide containing formulation provided the highest visible light blocking abilities compared to the other inorganic pigments tested (i.e., barium sulfate, silica, and bismuth oxychloride), and the mica-containing formulation was nearly as high as and comparable to the visible sunscreen cream, which contained almost twice the amount of iron oxide. When considering the entire visible light range of 400-800 nm, the mica-containing formulation has the highest protection factor and percent visible light blockage of all of the formulations tested, with barium sulfate being the second best performer. The bismuth oxychloride formulation, which had 4.4% mica and 3.9% bismuth oxychloride, performed worse than any of the tested formulations and similar to the control formulation with no visible light blocking additives. Therefore, without wishing to be bound by theory, it appears that some incompatibility may occur between the mixture of mica and bismuth oxychloride.

HDRS SPF, UVA-PF, CW, and UVA1/UV Calculations: Knowledge of the spectral shape of the sunscreen compositions throughout the UV spectrum, combined with the HDRS measurements of the UVA-PF, allows for similar hybrid calculations to estimate a composition's SPF, UVA-PF, Critical Wavelength, and UVA1/UV ratio. Using computations as described in the Cosmetics Europe HDRS test method (Cosmetics Europe Recommendation No 26 On the Use of Alternative Methods to ISO14444: Annex II HDRS Method Protocol, Mar. 23, 2022), the following SPF, UVA-PF, Critical Wavelength, and UVA1/UV ratios were calculated for each formulation and are shown in Table 4 below.

yielding a Critical Wavelength value similar to all of the other tested formulations, as well as superior visible light protection.

The barium sulfate and silica additives boosted both SPF and UVA-PF values as compared to the 0322A Control, while the bismuth oxychloride/mica formulation had a similar SPF and statistically higher UVA-PF. The visible sunscreen cream had the highest UVA-PF values, which may be attributed to the presence of 10% zinc oxide. The HDRS measured SPF was in line with the actual static SPF for the visible sunscreen cream, which tested at SPF 60 in vivo.

From these experiments, it is concluded that the addition of mica to a titanium dioxide and iron oxide formulation provided the greatest boost of SPF and visible light protection, but not UVA-PF. Barium sulfate and silica also provided significant boosts of SPF, UVA-PF, and visible light protection. However, the combination of mica and bismuth oxychloride was not additive and provided only slightly improved UVA protection with no significant increase in visible light protection.

Example 2

Anhydrous sunscreen stick formulations containing inorganic sunblock filters and visible light protecting agents were evaluated for their ability to protect against both UV

TABLE 4

| | | | | | |
|---|---|---|---|---|---|
| | | SPF, UVA-PF, Critical Wavelength, and UVA1/UV ratios | | | |
| | 0322A Control | 0211A (+Barium Sulfate) | 0211B (+Silica) | 0211D (+Bismuth oxychloride and mica) | 0314A (+Mica) | 137-1216A Visible Light Sunscreen |
| SPF | 42.4 | 71.5* | 60.7* | 47.1 | 80.2* | 54.5 |
| UVA-PF | 12.3 | 17.7* | 15.8** | 15.6* | 14.2 | 23.0* |
| CW (nm) | 379.35 | 379.36 | 379.15 | 379.9 | 380.19 | 380.77 |
| UVA1/UV | 0.76 | 0.77 | 0.77 | 0.79 | 0.73 | 0.84 |

*Values were statistically greater than the 0322A Control formulation ($p < 0.05$).
**As compared to 0322A Control formulation, values had $p > 0.05$ but $<0.1$.

As shown in Table 4 above, the barium sulfate additive yielded significantly higher SPF and UVA-PF values as compared to the 0322A Control formulation, while the silica additive had trending values with $p>0.05$ but $<0.1$. Mica showed the highest SPF, but the lowest UVA-PF with a relatively low mid-UVA absorbance. The mica additive did show longer UVA wavelength absorbance (380-390 nm), and visible light radiation. The experiment was also designed to evaluate the ability of barium sulfate and mica to add visible light protection, both alone and in combination.

The test materials included 12 inorganic stick formulations, and one organic sunscreen formulation. The 13 formulations were as shown in Table 5 below.

TABLE 5

| | Test Sunscreen Formulations | | | | | | |
|---|---|---|---|---|---|---|---|
| | #1 0322A Control | #2 0523A | #3 0525A | #4 0525B | #5 0519A | #6 0520A | #7 0512A |
| Titanium Dioxide (75% nano, 25% micron) | 23.5% | 13.3% | 13.3% | 13.3% | 12.5% | 12.5% | 12.5% |
| Zinc Oxide | — | 7.5% | 7.5% | 7.5% | 11% | 11% | 11% |
| Iron Oxide | 2.75% | 2.75% | 2.75% | 2.75% | 2.75% | 2.75% | 2.75% |
| Barium Sulfate | — | 7.5% | — | 3.5% | 5% | — | 2.5% |
| Mica | — | — | 7% | 3.5% | — | 5% | 2.5% |

TABLE 5-continued

| | Test Sunscreen Formulations | | | | | |
|---|---|---|---|---|---|---|
| | #8 0510A | #9 0502A | #9a 0517A | #9b 0516A | #10 0517B | #11 0923A |
| Titanium Dioxide (75% nano, 25% micron) | 12.5% | 12.5% | 12.5% | 12.5% | 12.5% | — |
| Zinc Oxide | 11% | 11% | 11% | 11% | 11% | — |
| Iron Oxide | 2.0% | 1.0% | 0.5% | — | 4.5% | — |
| Barium Sulfate | 2.5% | 2.5% | 2.5% | 2.5% | — | 2.5% |
| Mica | 2.5% | 2.5% | 2.5% | 2.5% | — | — |
| Other | — | — | — | — | — | Organic UV filters |

All of the formulations listed above in Table 5 with the exception of #11 (0923A) were anhydrous stick based compositions that further comprised C12-15 alkyl benzoate, beeswax, butyloctyl salicylate, copernica cerifa (carnauba) wax, aluminum hydroxide, tocopheryl acetate, triethoxycapryilsilane, isohexadecane, caprylic/capric triglyceride, shea butter, triacontanyl PVP, and stearic acid.

In Vitro UV and Visible Spectrophotometric Assessment at 290-800 nm and HDRS: The UV and visible light absorption spectrum of the sunscreen formulations set forth above in Table 5 were evaluated in vitro using conventional thin film spectrophotometry according to the methodology set forth above in Example 1. The HDRS measurements of the UVA-PFs of the sunscreen formulations were conducted as described above in Example 1, using a Solar Light Polychromatic HDRS device, and the UVA-PFs of each formulation as measured by HDRS was calculated, as well as the UVA-PFs of the in vitro spectra. The in vitro spectral absorbance values (290-800 nm) were multiplied by a single numerical factor "s" to scale the in vitro spectra to yield a UVA-PF identical to the HDRS determined UVA-PF, and the results are shown in FIGS. 2-4.

Figure 2:
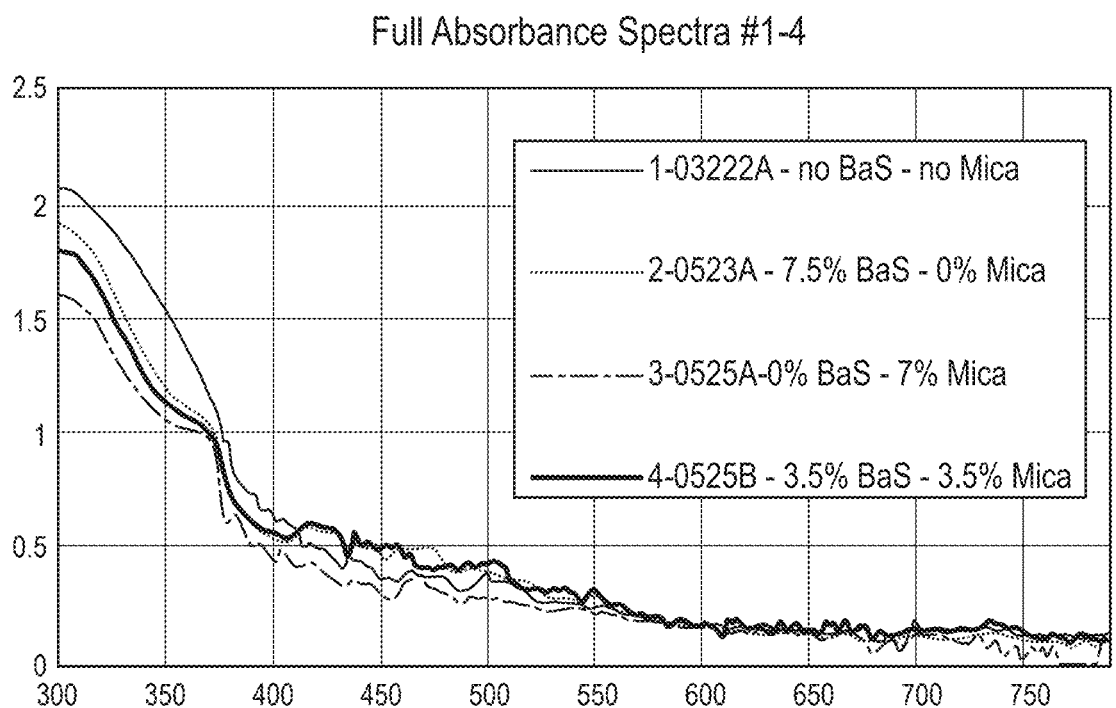
FIG. 2 is a graph showing the absorbance of four sunscreen formulations #1, #2, #3, and #4, as described in Example 2, across the UV and visible light spectrum (300-800 nm) of the electromagnetic spectrum.

FIG. 2 shows the full absorbance spectra for formulations #1-4 described in Table 5. The control formulation #1 has a high titanium dioxide content with no zinc oxide or other additives; formulation #2-4 contain a lower amount of titanium dioxide, but 11% zinc oxide, where #2 contains 7.5% barium sulfate and no mica, #3 contains 7% mica and no barium sulfate, and #4 contains 3.5% barium sulfate and 3.5% mica. As shown in FIG. 2, formulae #2 and #4 had a higher level of visible light blockage in the 400-500 nm visible light range than formula #1. Although the formulation with mica alone (#3) showed no significant added visible light protection, when combined with barium sulfate at 3.5% each (formula #4) the protection was similar to the protection afforded by formula #2, containing 7.5% barium sulfate.

Figure 3:
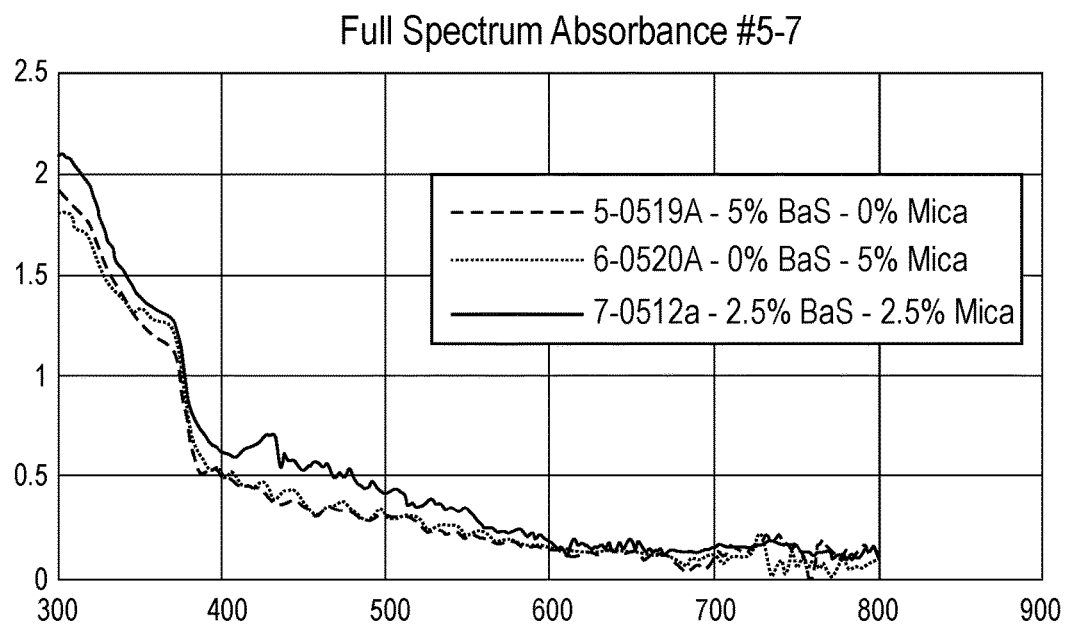
FIG. 3 is a graph showing the absorbance of four sunscreen formulations #5, #7, #8, and #9, as described in Example 2, across the UV and visible light spectrum (300-800 nm) of the electromagnetic spectrum.

FIG. 3 shows the full absorbance spectra for formulations #5-7 described in Table 5. As shown, a synergistic combination was observed when both barium sulfate and mica were included as visible light blocking additives in the formulation #7. Additionally, an improved UV absorption is seen in the visible range, e.g., between 400-550 nm for this formulation. The synergistic protection offered by the combination of barium sulfate and mica is seen wherein each additive by itself at 5% has similar visible light protection, yet the combination of barium sulfate and mica at 2.5% each offered greater protection than either alone.

Figure 4:
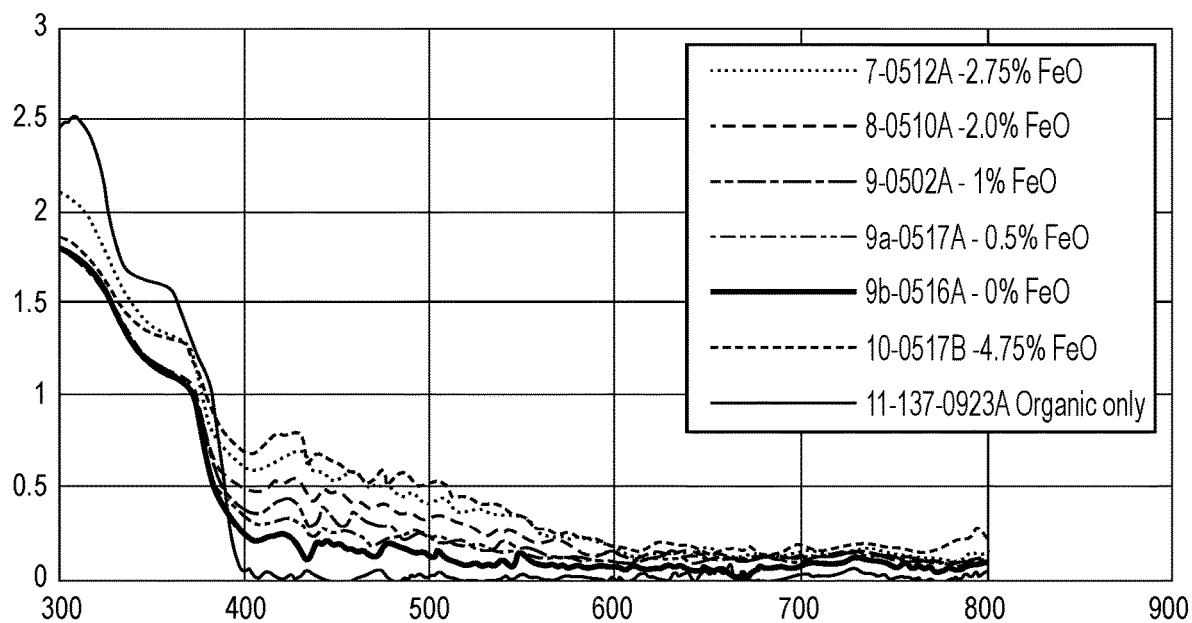
FIG. 4 is a graph showing the absorbance of seven sunscreen formulations #7, #8, #9, #9a, #9b, #10, and #11, as described in Example 2, across the UV and visible light spectrum (300-800 nm) of the electromagnetic spectrum.

FIG. 4 shows the full absorbance spectra for formulations #7-11, illustrating a dose-response in protection offered by iron oxide in decreasing amounts of 4.75% (#10), 2.75% (#7), 2.0% (#8), 1% (#9), 0.5% (#9a), and 0% (#9b). The increasing visible light protection offered by increasing amounts of iron oxide is compared to the lack of visible light protection observed by a sunscreen formulation containing only organic UV filters (#11). FIG. 4 thus illustrates that a factor of visible light protection is the iron oxide concentration.

Both VL-PFS and the percent of visible light blocked by the sunscreen formulations were calculated using the formulae described in Example 1 and are shown below in Tables 6 and 7, respectively.

TABLE 6

| | Visible Light Protection Factors | | | | | | |
|---|---|---|---|---|---|---|---|
| | #1 0322A Control | #2 0523A | #3 0525A | #4 0525B | #5 0519A | #6 0520A | #7 0512A |
| 400-500 nm | 2.70 | 3.15 | 2.36 | 3.17 | 2.35 | 2.46 | 3.65 |
| 400-600 nm | 2.18 | 2.40 | 1.95 | 2.44 | 1.94 | 2.04 | 2.71 |
| 400-800 nm | 1.60 | 1.67 | 1.50 | 1.70 | 1.48 | 1.54 | 1.79 |
| | #8 0510A | #9 0502A | #9a 0517A | #9b 0516A | #10 0517B | #11 0923A | |
| 400-500 nm | 2.76 | 2.15 | 1.84 | 1.54 | 4.38 | 1.03 | |
| 400-600 nm | 2.17 | 1.76 | 1.58 | 1.37 | 3.09 | 1.02 | |
| 400-800 nm | 1.57 | 1.39 | 1.31 | 1.21 | 1.93 | 1.02 | |

TABLE 7

Percent of Visible Light Blocked

|  | #1 0322A Control | #2 0523A | #3 0525A | #4 0525B | #5 0519A | #6 0520A | #7 0512A |
|---|---|---|---|---|---|---|---|
| 400-500 nm | 63% | 68% | 58% | 68% | 57% | 59% | 73% |
| 400-600 nm | 54% | 58% | 49% | 59% | 49% | 51% | 63% |
| 400-800 nm | 38% | 40% | 33% | 41% | 32% | 35% | 44% |

|  | #8 0510A | #9 0502A | #9a 0517A | #9b 0516A | #10 0517B | #11 0923A |
|---|---|---|---|---|---|---|
| 400-500 nm | 64% | 54% | 46% | 35% | 77% | 3% |
| 400-600 nm | 54% | 43% | 37% | 27% | 68% | 2% |
| 400-800 nm | 36% | 28% | 24% | 18% | 48% | 2% |

Figure 5:
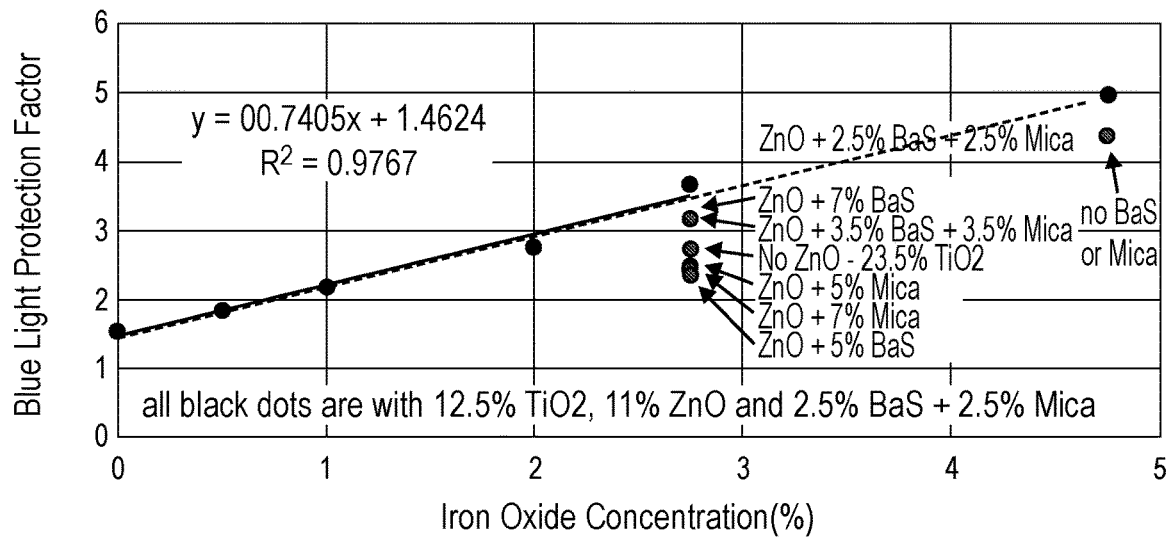
FIG. 5 is a graph illustrating the dose response of blue light (about 400-500 nm) protection as it relates to the iron oxide concentration of the sunscreen formulations as described in Example 2.

FIG. 5 is a graph illustrating the dependence of the VL-PF [Blue Light Protection Factor (400-500 nm)] on the iron oxide concentration in the formulations. In FIG. 5, the first five data points (from left to right) represent formulations #9b, 9a, 9, 8, and 7, all of which contain 2.5% barium sulfate and 2.5% mica, but containing decreasing amounts of iron oxide. The amount of blue light protection increases as the amount of iron oxide in the formulation increases. The data point furthest to the right/top represents the projected protection factor for a formulation containing 4.75% iron oxide, 2.5% barium sulfate, and 2.5% mica, based on the regression of the first 5 data points. The data point below the projected protection factor data point is the data point for formulation #10, containing 4.75% iron oxide but no barium sulfate or mica. The difference between the projected data point and that for formulation #10 is the estimated additional protection provided by the barium sulfate/mica combination, equivalent to an additional protection factor of about 0.4 protection factor units. Evaluating the visible light protection illustrates that the predominant protection element in the formulations is iron oxide, wherein when the iron oxide concentration is varied from 4.75% to 0%, the blue light protection factor drops from 77% to 35%.

Figure 6:
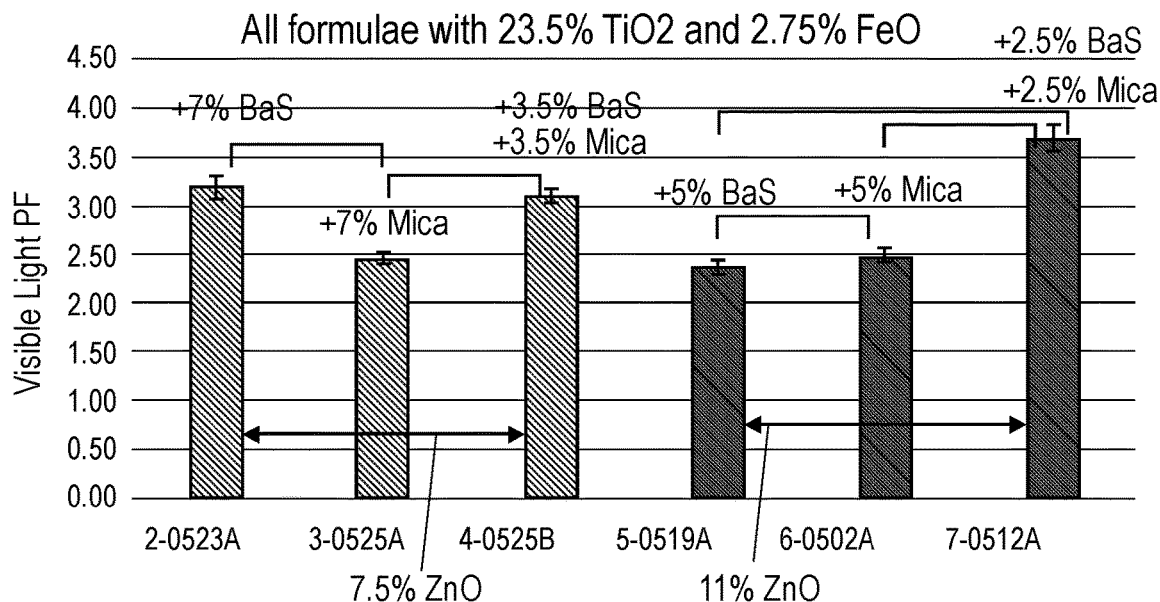
FIG. 6 is a bar graph illustrating the blue light protection factor of sunscreen formulations #2, #3, #4, #5, #6, and #7, as described in Example 2. The error bars indicate a CI=95%, and the brackets above the bars indicate statistical significance, wherein $p<0.01$ for formulation #2 compared to #3 and $p<0.1$ for formulations #3 versus #4. Likewise, $p<0.011$ for formulation #5 compared to #6, and $p<0.01$ for formulation #7 versus either formulation #5 or #6.

FIG. 6 further illustrates the synergistic combination of barium sulfate and mica to provide greater blue light protection in a sunscreen formulation. Formulations #2, 3, and 4 show a slight addition to blue light protection with both barium sulfate and mica (#4, 3.17 at 400-500 nm) as compared to barium sulfate alone (#2, 3.15 at 400-500 nm), and a modest addition to blue light protection with mica alone (#3, 2.36 at 400-500 nm). Notably, formulations #5, #6, and #7 show a synergistic increase in blue light protection with both barium sulfate and mica (#7, 3.65 at 400-500 nm) as compared to either barium sulfate alone (#5, 2.35 at 400-500 nm) or mica alone (#6, 2.46 at 400-500 nm). This synergistic increase in protection is observed throughout the entire visible light spectra of 400-800 nm.

Hybrid calculations were made as discussed above in Example 1 to estimate the SPF, UVA-PF, Critical Wavelength, and UVA1/UV ratios of each of the formulations tested. Using the computations described in the Cosmetics Europe HDRS test method, the results shown in Table 8 below were calculated:

TABLE 8

Estimated SPF, UVA-PF, CW, UVA1/UV, and VL-PF for Formulations

|  | #1 0322A Control | #2 0523A | #3 0525A | #4 0525B | #5 0519A | #6 0520A | #7 0512A |
|---|---|---|---|---|---|---|---|
| SPF | 82.2 | 56.7 | 52.6 | 45.8 | 56.4 | 49.1 | 85.5 |
| UVA-PF | 18.9 | 12.3 | 11.6 | 11.3 | 12.8 | 14.3 | 18.1 |
| CW | 378.35 | 377.49 | 376.72 | 378.73 | 375.7 | 376.5 | 377.83 |
| UVA1/UV | 0.76 | 0.73 | 0.72 | 0.74 | 0.73 | 0.77 | 0.75 |
| VL-PF | 2.70 | 3.15 | 2.36 | 3.17 | 2.35 | 2.46 | 3.65 |

|  | #8 0510A | #9 0502A | #9a 0517A | #9b 0516A | #10 0517B | #11 0923A |
|---|---|---|---|---|---|---|
| SPF | 45.8 | 49.9 | 49.6 | 45.3 | 54.6 | 184.9 |
| UVA-PF | 11.8 | 11.4 | 10.7 | 10.6 | 17.6 | 23.7 |
| CW | 377.02 | 375.06 | 374.04 | 373.44 | 380.85 | 372.79 |
| UVA1/UV | 0.74 | 0.72 | 0.7 | 0.71 | 0.8 | 0.7 |
| VL-PF | 2.76 | 2.15 | 1.84 | 1.54 | 4.38 | 1.03 |

Figure 7:
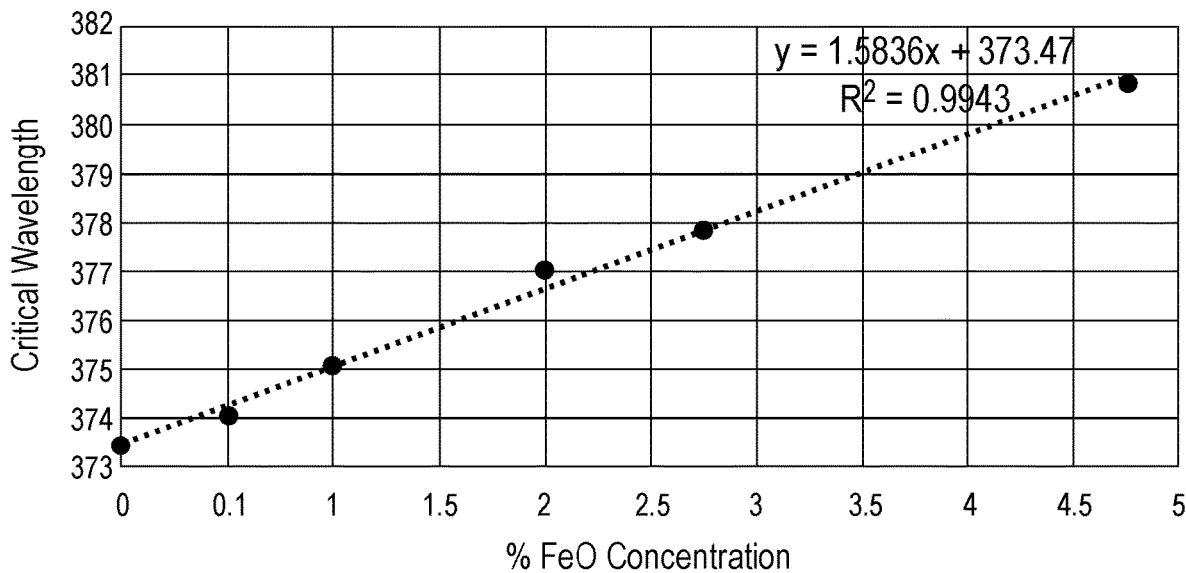
FIG. 7 is a graph illustrating the critical wavelength dependence on the iron oxide concentration of the sunscreen formulations #9b, #9a, #9, #8, #7, and #10 (in order of increasing iron oxide concentration), as described in Example 2.

It is noted that the calculated values for SPF and UVA-PF for formulation #11 are likely inflated as they do not include the effects of photostability on the expected SPF outcomes. As shown in Table 8 and FIG. 7, in addition to the other calculated protection factor values, the critical wavelength is also dependent on the iron oxide content, wherein increasing amounts of iron oxide results in an increased critical wavelength.

Example 3

The UV and visible light blocking properties of individual ingredients used in stick and cream sunscreen formulations was evaluated. Twelve formulations comprising individual ingredient sunblocking actives were prepared as set forth in Table 9 below.

TABLE 9

Individual Sunblocking Active Ingredient Formulations

| Formulation | TiO₂ (nano) | TiO₂ (micron) | ZnO | Fe₂O₃ | BaS | Mica/ TiO₂ | TiO₂ |
|---|---|---|---|---|---|---|---|
| #1121 | 12.5% | | | | | | |
| #1123A | | 12.5% | | | | | |
| #1123B | | | 11% | | | | |
| #1205A | | | | 1% | | | |
| #1205B | | | | 2.75% | | | |
| #1205C | | | | 4.5% | | | |
| #1122A | | | | | 2.5% | | |
| #1122B | | | | | 5% | | |
| #1213A | | | | | | 2.5%/2.2% | |
| #1213B | | | | | | 5%/4.4% | |
| #1212A | | | | | | | 2.2% |
| #1212B | | | | | | | 4.4% |

In Vitro UV and Visible Spectrophotometric Assessment—290-800 nm

The UV and visible light absorption spectrum of the 12 test sunscreen preparations were evaluated in vitro using conventional thin film spectrophotometry similar to that used for the FDA Critical Wavelength test (FDA Sunscreen Monograph: Labeling and Effectiveness Testing: Sunscreen Drug Products for Over-the-Counter Human Use. Federal Register 2011, 76:117, 35661-35665) and ISO24443 in vitro UVA protection standard (ISO24443 Determination of sunscreen UVA protection in vitro 2021). Helioscreen HD6 Polymethylmethacrylate (PMMA) plates were individually weighed, tared, smeared with test product, and rubbed by finger to a uniform film resulting in a total weight per unit area of 1.2 mg/cm$^1$. Three blank control PMMA plate were prepared with glycerin application. An Optronics 756 spectroradiometer with a 6" integrating sphere entrance port was used for the spectral scans of the control PMMA plates, and each of the sunscreen treated plates. A Labsphere spectrophotometer was used to scan absorbance values from 290-450 nm. The baseline was measured from 290-800 nm first with the glycerin treated control PMMA plates with the Labsphere spectrophotometer, and then each of the sunscreen-prepared PMMA plates were scanned at 9 locations. The absorbance was also measured across the upper UV and across the visible spectrum using a OL756 spectroradiometer by first measuring the output of the tungsten lamp through glycerin treated plates (baseline), and then through the sunscreen treated plates. Absorbance was calculated by the equation: $A=-\log(I_{SS\ treated}/I_{blank})$, where $I_{SS\ treated}$ was irradiance of the tungsten lamp with the sunscreen treated PMMA plate over the entrance port, and $I_{blank}$ was the irradiance of the solar simulator with the glycerin treated PMMA plate over the entrance port. The spectra from the two absorbance devices were overlayed and normalized in the common wavelength regions to provide a continuous absorbance value from 290-700 nm. Noise "ripple" in the scans were smoothed with an exponential smoothing function.

Figure 8:
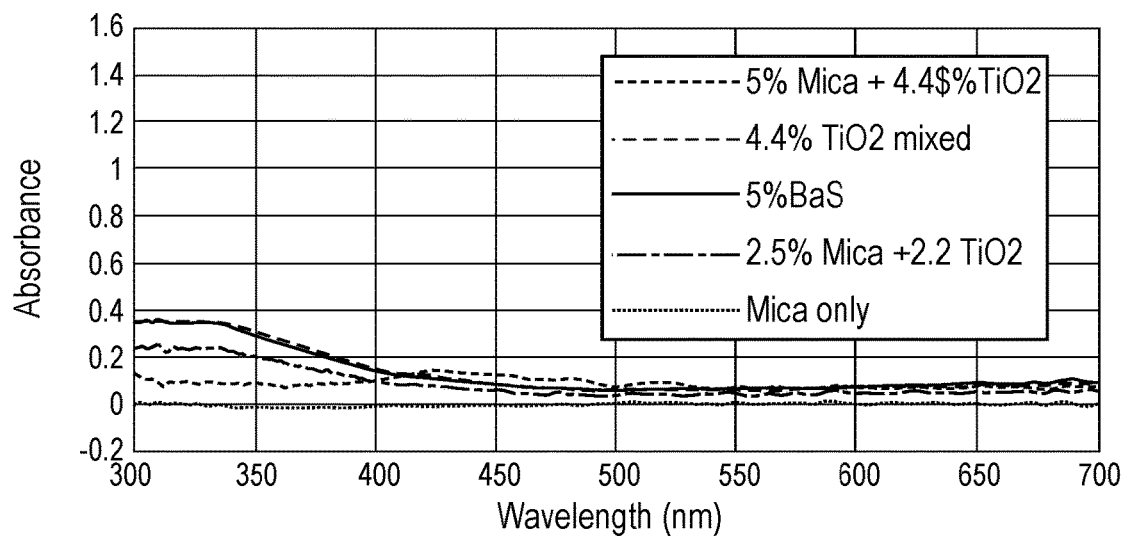
FIG. 8 is a graph showing the absorbance of four sunscreen formulations #1213A, #1213B, #1122B, and #1212B, as well as the absorbance resulting from mica alone, wherein 4.4% $TiO_2$ spectrum has been subtracted, as described in Example 3, across the UV and visible light spectrum (300-700 nm) of the electromagnetic spectrum.

Hybrid Diffuse Reflectance Spectroscopy (HDRS)—HDRS measurements of the UVA-PFs of the test products were conducted using a Solar Light Polychromatic HDRS device, and the UVA-PF was calculated for using Formula 1 as set forth above in Example 1. The in vitro spectral absorbance values (290-800 nm) were multiplied by single numerical factor "s" to scale the in vitro spectra to yield a UVA-PF identical to the HDRS determined UVA-PF, providing absolute absorbance spectra. FIG. 8 shows the absorbance properties of the mica and barium sulfate additives. It is noted that in FIG. 8, when the 4.4% TiO₂ absorbance is subtracted from the Mica+4.4% TiO₂ spectrum, the resulting absorbance of the Mica by itself is virtually zero across the spectrum. The barium sulfate at 5% has a very low absorbance value, averaging around 0.1 AU across the spectrum. These data indicate that the highest contribution of the BaS is 0.1 AU, and the mica contribution is zero across the spectrum. However, when combined in a complete formulation (e.g., Formula #7 in Example 1 above), the visible light protection was synergistically higher than either of them alone at 5% concentrations. While not wishing to be bound by theory, the explanation may lie in the physical interactions of the BaS and the Mica+TiO₂ with the nano TiO₂ and ZnO in the complete formulation, giving better separation of the agglomerates and a more complete coverage of the particles on skin.

Example 4—Natural Sunlight SPF Test of 4 Sunscreens in Arequipa, Peru

Formulations of four different sunscreens was SPF tested in tropical, mid-day natural sunlight. The tests were conducted using methods similar to the FDA sunscreen final rule, except that natural sunlight was used instead of a solar simulator.

Subjects: Ten subjects having Fitzpatrick skin Type I (2 subjects), II (6 subjects), and III (2 subjects) were enrolled in the study; no subjects were pregnant, had a history of skin cancer, or were otherwise disqualified.

Sun exposures and conditions: Subjects were exposed to 3942+/−5 J/m² of erythema effective energy (17.8× minimal erythema dose (MED) for a Type II individual or 37.6 SEDs) and 60.3+/−1 J/cm² UVA of outdoor natural sunlight in Arequipa, Peru (elevation 7800' at South Latitude of 16°) on cloudless days with full sky exposure over a period of 170 minutes centered on solar noon. Temperatures and humidity during the test periods were in the range of 70° to 71° with dew points 17°-37° (low humidity), approximating clinical laboratory conditions. The solar elevation angle ranged from 75° to 87.6° during the exposure periods.

Test products: Four stick products were formulated containing 12.5% titanium dioxide and 10.8% zinc oxide as the primary sunscreen active ingredients. The formulations also contained varying concentrations of iron oxide, ranging from 0 (control) to 4% (dark), as set forth in Table 10 below.

TABLE 10

Concentration of ingredients in test formulations (% w/w)

| | #1216A Control (C) | #0817A Light (L) | #1025A Medium (M) | #0517B Dark (D) |
|---|---|---|---|---|
| TiO₂ | 12.5 | 12.5 | 12.5 | 12.5 |
| ZnO | 10.8 | 10.8 | 10.8 | 10.8 |
| Fe₂O₃ | 0 | 1 | 2.75 | 4.0 |
| BaS | 0 | 2.5 | 2.5 | 0 |
| Mica | 0 | 2.5 | 2.5 | 0 |

The stick were warmed to liquid form and pipetted volumetrically to achieve an application density of 2 mg/cm² of product on the skin and allowed to dry for at least 15 minutes. Aluminum laminated templates were adhered to each subject's back and both control and test sunscreens with defined circular exposure sites, and the remainder of the back, legs, arms and heads were covered with sun protective clothing and a hat. Each group of subjects was exposed to the sun simultaneously.

Subjects were exposed to a maximum of 170 minutes of mid-day sun centered on solar noon. They were instructed to lay as motionless as possible with their backs facing the sun. Test sites were covered using aluminum tape based upon pre-arrange sun exposure doses (Erythema weighted UVB doses). The sunburning UV intensities and UVA intensities of the sun were measured each minute, and integrated doses were calculated over the exposure period using a Solar Light Model PMA2100 Radiometer with and PMA2101 erythema sensor and a PMA2110 UVA sensor. Control unprotected subsites were covered at pre-set intervals 25% over the first 45 minutes to determine the unprotected Minimal Erythema and Minimal Pigment Darkening Doses. Exposures subsites for the sunscreen treated areas were also covered at pre-determined doses to estimate Minimal Erythema and Minimal Pigment Darkening Doses for the protected sites.

Grading: A trained and unbiased grader, blinded to the treatment locations (except for the unprotected MED), evaluated the unprotected and protected skin sites for erythema and PPD sun reactions the next morning, 16-24 hours after the sun exposure. Erythema responses and Persistent Pigmentation responses were graded separately. To distinguish between the two responses, if both were present, light pressure was applied to the test subsite, and if no difference was seen in the subsite, then the response was only a Persistent Pigment response. If blanching was also observed, then erythema was scored. If only erythema was seen, then no Persistent Pigmentation was scored as 0.

The following erythema grading scale was used:
0=No perceptible erythema or PPD
0.5=Ambiguous erythema or PPD without clearly defined borders
1=Unambiguous erythema or PPD with clearly defined borders (MEDu or PPD-Pfu)
2=Strong perceptible erythema or PPD
3=Strong erythema or PPD with edema The protected and unprotected skin sites were graded and photographed between 16 and 24 hours of sun exposure. The 8 unprotected skin sites were visible on the left side in a vertical line of each subject's back. Each of the 4 sunscreen test areas (30 cm 2) was to the right of or just below the unprotected sites. Each of the 6 sunscreen subsites that was covered progressively from bottom left to bottom right and then top left to top right based upon the Principal Investigator's direction when pre-determined accumulated erythema weighted UV doses were reached using the calibrated radiometers. The erythema reaction for each sunscreen site progressed in sequence of redness (erythema) based upon accumulated sun exposure. The grading results are shown below in Table 11.

TABLE 11

Erythema grades recorded for 4 sunscreen test products on 10 test subjects

| Erythema Grade | #1216A Control (C) | #0817A Light (L) | #1025A Medium (M) | #0517B Dark (D) |
|---|---|---|---|---|
| 2 | 4 | 0 | 0 | 0 |
| 1 | 5 | 6 | 4 | 4 |
| 0.5 | 0 | 3 | 1 | 2 |
| 0 | 1 | 1 | 5 | 4 |
| Median | 1 | 1 | 0.25 | 0.5 |

Although all formulations were not statistically different from each other, The Light, Medium, and Dark formulations were statistically different from the Control (p<0.05). Surprisingly, the median value for the medium tint, which also contained mica and barium sulfate as well as 2.75% iron oxide, was higher than the dark tinted product containing a higher 4.00% iron oxide content.

The SPFs were calculated by dividing each subject's unprotected MED by the sunscreen protected MED. For subjects with no erythema responses at the highest dose, a minimum SPF value was calculated using the highest protected MED value. SPFs were not determined on the Control formulation due to lack of available area on test subject's backs; only the top exposure dose was evaluated as described above. The results are shown in Table 12 below.

TABLE 12

Minimum derived SPF values and Minimum derived PPD-PF values for 10 test subjects

| | Minimum derived SPF values | | | Minimum derived PPD-PF values | | |
|---|---|---|---|---|---|---|
| Subject (Fitzpatrick skin type) | #0817A Light (L) | #1025A Medium (M) | #0517B Dark (D) | #0817A Light (L) | #1025A Medium (M) | #0517B Dark (D) |
| 1 (III) | 12.9 | 12.9 | 12.9 | 6.6 | 10.5 | 10.5 |
| 2 (I) | ≥18.7 | ≥18.7 | ≥18.8 | NA | NA | NA |
| 3 (III) | ≥14.2 | 8.0 | ≥14.2 | 6.6 | 6.6 | ≥18.6 |
| 4 (II) | 9.1 | ≥16.1 | 12.9 | 10.6 | 10.6 | 10.6 |
| 5 (I) | 12.9 | ≥22.1 | ≥22.9 | 13 | ≥18.6 | ≥18.6 |
| 6 (II) | 15 | ≥18.7 | 8.5 | 15.4 | ≥15.4 | 15.4 |
| 7 (II) | 12.9 | 12.9 | ≥22.9 | 8.5 | ≥15.4 | ≥15.4 |
| 8 (II) | 8.4 | 10.4 | 12.9 | 6.8 | 8.5 | 8.5 |
| 9 (II) | ≥18.8 | ≥18.7 | ≥18.7 | 13 | ≥18.6 | ≥18.6 |
| 10 (II) | ≥22.9 | ≥22.9 | ≥22.9 | ≥24.3 | 24.3 | 24.3 |
| Minimum Sverage | 14.6 SD 4.5 | 16.2 SD 5.1 | 16.8 SD 5.2 | 11.5 SD 5.9 | 14.3 SD 5/7 | 15.6 SD 5.1 |

While the SPF values may appear to be low compared with currently marketed products, the difference may be attributed to the light source utilized to test commercially marketed products. Commercial products are tested using a simulated sun source, which is devoid of long wavelength UVA1 and completely devoid of visible light. Previous testing has shown that the FDA and ISO Reference Standard P2 sunscreen (SPF 16.3 in simulated sunlight clinical testing) is only SPF 4.5 in natural sunlight.

Similarly, the ISO Reference Standard P8.5 sunscreen (SPF 63 in simulated sunlight clinical testing) is only SPF 8 in natural sunlight under similar conditions as those reported in the present Example. Therefore, attaining SPFs above SPF 10 in natural sunlight is unusual and remarkable. The difference is attributable to the erythema contributions to the erythema responses coming from the longwave UVA and visible light portions of natural sunlight that is unprotected using UV-only blocking filters.

Similar to SPF for erythema protection, Pigment Darkening Protection Factor (PPD-PF) provides a similar protection value against pigment darkening (tanning) of the skin. The PPD-PF is the ratio of the minimum dose required to induce a unambiguous pigment darkening response of unprotected skin at 24 hours after exposure, divided by the minimum dose for unambiguous pigment darkening of sunscreen protected skin at the same time point. This is analogous to the UVA-PF tested clinically using only UVA radiation, but in this case the entire solar spectrum is utilized including UVB, UVA and visible (and IR) radiation.

PPD-PF for the test subjects was calculated, and the results are shown in Table 12 above. Statistical analysis using Student's T-test indicated no significant difference between the Dark and Medium formulations (p=0.17); however, there were statistical differences between both the Medium and Light formulations, as well as between the Dark and Light formulations (p=<0.015 and p<0.01, respectively).

Demonstrating Visible Light Protection of Test Formulations: To demonstrate that the difference in protection was attributable to the visible portion of natural sunlight, additional subjects were tested wherein CGA 400 longpass filters were placed over sunscreen protected sites to block all ultraviolet radiation below 400 nm, only allowing visible and infrared light to illuminate the sunscreen protected skin. Thus any discernable differences in protection by the test formulations would be attributable to differences in the visible light protection. Test formulations Medium and Control were chosen to demonstrate this.

Formulations Medium and Control were applied to the skin in two separate but adjacent sites (catty-cornered). In each subject, it was demonstrated that the site treated was the Control formulation has a stronger and more visible reaction than the site treated with the Medium formulation.

Example 5—Evaluation of Sunscreen Visibility on Skin

The objective of the evaluation was to assess the visibility of sunscreens on skin using instrumental evaluations. The results demonstrate that sunscreen containing a combination of mica and barium sulfate has a lower visibility on the skin at 2.75% iron oxide compared to a sunscreen without mica and barium sulfate having 4.5% iron oxide; nonetheless, both compositions provide similar visible light protection.

Tests sites on human skin included the dorsal forearm (darkest), the volar forearm, and the upper thigh (lightest). The three sites with differing background color were measured using a Chromameter CR-400A skin reflectance spectrometer before and after sunscreen application using the L a*b color space. Sunscreens were applied to the test skin sites at a controlled application density of 2 mg/cm², and the change in visibility was calculated using the formula for ΔE, wherein $$\Delta E = \sqrt{((\Delta L^2)+(\Delta a^2)+(\Delta b^2))},$$

where ΔE is the CIE definition of differences between two color measurements (i.e., the color difference before and after sunscreen application). ΔL is the difference in the L color space coordinate (black—white axis); Δa is the difference in the a* space coordinate (red-green axis); and Δb is the difference in the b* space coordinate (blue-yellow axis).

The following formulations five formulations were evaluated, as shown in Table 13 below.

TABLE 13

Formulations for skin visibility testing

| | Formulation % ingredient by weight | | | | |
|---|---|---|---|---|---|
| Ingredient | #1 | #2 | #3 | #4 | #5 |
| TiO₂ | 12.5% | 12.5% | 12.5% | 12.5% | 12.5% |
| ZnO | 10.8% | 10.8% | 10.8% | 10.8% | 10.8% |
| Fe₂O₃ | — | 1.0% | 2.75% | 2.75% | 4.5% |
| Mica | — | 2.5% | — | 2.5% | — |
| BaS | — | 2.5% | — | 2.5% | — |

Photos of the test sites made clear that Formulation #2 was the closest match to the background skin of the test subject and had the lowest calculated visibility after the sunscreen application. The ΔE values were calculated for each of the five formulations. The lower the calculated ΔE value, the lower the change in visibility is after application of sunscreen as compared to untreated skin. Each of the formulations were statistically different from the other on all three test sites (p<0.05). The ΔE values for each of the three test sites are shown below in Table 14.

TABLE 14

Average ΔE values for skin visibility testing (n = 3)

| Formulation | #1 | #2 | #3 | #4 | #5 |
|---|---|---|---|---|---|
| Dorsal Forearm | 13.645 | 3.5334 | 2.5872 | 5.2080 | 7.6801 |
| Volar Forearm | 7.4858 | 2.6528 | 6.6611 | 9.7941 | 11.5335 |
| Upper Thigh | 12.0237 | 5.1198 | 9.6516 | 13.6768 | 14.3893 |
| Average | 11.0518 | 3.7684 | 6.3000 | 9.5600 | 11.2010 |

The results demonstrate that the addition of mica and barium sulfate to the 2.75% iron oxide (Formulation #4) did increase the visibility as compared to a formulation with the same iron oxide content but without mica and barium sulfate (Formulation #3). Nonetheless, Formulation #4 was lower in visibility as compared to Formulation #5, while still providing comparable sunscreen protection to Formulation #5 as demonstrated in the Examples above, including in the outdoor sunscreen testing.

What is claimed is:

1. A method of reducing or preventing sunburn caused from visible light and ultraviolet (UV) radiation in a subject, comprising topically applying to the subject a sunscreen composition comprising:
   (a) at least two inorganic UV filtering agents comprising zinc oxide and titanium dioxide;
   (b) at least one inorganic pigment selected from iron oxide; and
   (c) at least two visible light protecting agents comprising barium sulfate and mica;

wherein the at least two visible light protecting agents are present in an amount effective to reduce or prevent sunburn caused from visible light;

wherein the at least two inorganic UV filtering agents are present in a total amount of about 10% to about 30%, by weight based on the total weight of the sunscreen composition; and wherein the at least two visible light protecting agents are present in a total amount of about 1% to about 10%, by weight based on the total weight of the sunscreen composition.

2. The method according to claim 1, wherein the sunscreen composition comprises zinc oxide present in an amount ranging from about 5% to about 15%, by weight based on the total weight of the sunscreen composition and titanium dioxide present in an amount ranging from about 5% to about 15%, by weight based on the total weight of the sunscreen composition.

3. The method according to claim 1, wherein the sunscreen composition is anhydrous.

4. The method according to claim 1, wherein at least one of the at least two visible light protecting agents further comprises a silica coating.

5. The method according to claim 1, wherein the iron oxide is chosen from the group consisting of black iron oxide, brown iron oxide, red iron oxide, yellow iron oxide, and mixtures thereof.

6. The method according to claim 1, wherein the iron oxide is present in the sunscreen composition in a total amount ranging from about 1% to about 5% by weight relative to the total weight of the sunscreen composition.

7. The method according to claim 1, wherein the barium sulfate is present in amount ranging from about 0.1% to about 5%, based on the total weight of the composition.

8. The method according to claim 1, wherein the barium sulfate is present in an amount of about 2.5%, based on the total weight of the composition.

9. The method according to claim 1, wherein the mica is present in amount ranging from about 0.1% to about 5%, based on the total weight of the composition.

10. The method according to claim 1, wherein the mica is present in an amount of about 2.5%, based on the total weight of the composition.

11. The method according to claim 1, wherein both the barium sulfate and the mica are each present in an amount of about 2.5%, based on the total weight of the composition.

12. The method according to claim 1, wherein the titanium dioxide has a mean particle size ranging from about 5 nm to about 20 nm.

13. The method according to claim 1, wherein the zinc oxide has a mean particle size ranging from about 10 nm to about 100 nm.

14. The method according to claim 1, wherein the sunscreen composition does not comprise an organic UV filtering agent.

15. A method of increasing a visible light protection factor (VL-PF) of a sunscreen composition that comprises at least two inorganic UV filtering agents comprising zinc oxide and titanium dioxide and at least one inorganic pigment selected from iron oxide, the method comprising adding to the sunscreen composition at least two visible light protecting agents comprising barium sulfate and mica, wherein the at least two visible light protecting agents are present in the sunscreen composition in an amount effective to increase the VL-PF over an electromagnetic wavelength spectra spanning from about 400 nm to about 800 nm;

wherein the at least two inorganic UV filtering agents are present in a total amount of about 10% to about 30%, by weight based on the total weight of the sunscreen composition; and wherein the at least two visible light protecting agents are present in a total amount of about 1% to about 10%, by weight based on the total weight of the sunscreen composition.

16. The method according to claim 15, wherein the electromagnetic wavelength spectra spans from about 400 nm to about 500 nm.

17. The method according to claim 15, wherein the visible light protection factor is increased by an amount of at least about 0.5.

18. A sunscreen composition comprising:
(a) at least two inorganic UV filtering agents comprising zinc oxide and titanium dioxide;
(b) at least one inorganic pigment selected from iron oxide; and
(c) at least two visible light protecting agents comprising barium sulfate and mica;

wherein the at least two visible light protecting agents are present in an amount effective to reduce or prevent sunburn caused from visible light;

wherein the at least two inorganic UV filtering agents are present in a total amount of about 10% to about 30%, by weight based on the total weight of the sunscreen composition; and wherein the at least two visible light protecting agents are present in a total amount of about 1% to about 10%, by weight based on the total weight of the sunscreen composition.

19. The sunscreen composition according to claim 18, wherein the composition is anhydrous.

20. The sunscreen composition according to claim 18, wherein both the barium sulfate and the mica are each present in an amount of about 2.5%, based on the total weight of the composition.

\* \* \* \* \*